(12) United States Patent
Labgold et al.

(10) Patent No.: US 11,307,201 B2
(45) Date of Patent: *Apr. 19, 2022

(54) SELF-ACTUATING SIGNAL PRODUCING DETECTION DEVICES AND METHODS

(75) Inventors: Marc Robert Labgold, Reston, VA (US); George G Jokhadze, Menlo Park, CA (US)

(73) Assignee: RED IVORY LLC, Honolulu, HI (US)

( * ) Notice: Subject to any disclaimer, the term of this patent is extended or adjusted under 35 U.S.C. 154(b) by 1580 days.

This patent is subject to a terminal disclaimer.

(21) Appl. No.: 12/211,992

(22) Filed: Sep. 17, 2008

(65) Prior Publication Data

US 2009/0117574 A1 May 7, 2009

Related U.S. Application Data

(60) Provisional application No. 60/960,112, filed on Sep. 17, 2007, provisional application No. 61/123,280, filed on Apr. 7, 2008.

(51) Int. Cl.
*C12Q 1/68* (2018.01)
*G01N 33/543* (2006.01)
*C12Q 1/6825* (2018.01)

(52) U.S. Cl.
CPC ....... *G01N 33/5438* (2013.01); *C12Q 1/6825* (2013.01)

(58) Field of Classification Search
CPC .................................................. G01N 33/5438
See application file for complete search history.

(56) References Cited

U.S. PATENT DOCUMENTS

| | | |
|---|---|---|
| 3,941,135 A | 3/1976 | von Sturm et al. |
| 4,044,193 A | 8/1977 | Petrow et al. |
| 4,126,934 A | 11/1978 | Richter et al. |
| 4,166,143 A | 8/1979 | Petrow et al. |
| 4,224,125 A | 9/1980 | Nakamura et al. |
| 4,229,490 A | 10/1980 | Frank et al. |
| 4,293,396 A | 10/1981 | Allen et al. |
| 4,545,382 A | 10/1985 | Higgins et al. |
| 4,578,323 A | 3/1986 | Hertl et al. |
| 4,581,336 A | 4/1986 | Malloy et al. |
| 4,683,195 A | 7/1987 | Mullis et al. |
| 4,683,202 A | 7/1987 | Mullis |
| 4,703,017 A | 10/1987 | Campbell et al. |
| 4,711,245 A | 12/1987 | Higgins et al. |
| 4,855,240 A | 8/1989 | Rosenstein et al. |
| 4,970,145 A | 11/1990 | Bennetto et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,320,725 A | 6/1994 | Gregg et al. |
| 5,356,785 A | 10/1994 | McMahon et al. |
| 5,356,786 A | 10/1994 | Heller et al. |
| 5,468,648 A | 11/1995 | Chandler |
| 5,593,852 A | 1/1997 | Heller et al. |
| 5,656,503 A | 8/1997 | May et al. |
| 5,660,940 A | 8/1997 | Larsson et al. |
| 5,665,222 A | 9/1997 | Heller et al. |
| 5,766,961 A | 6/1998 | Pawlak et al. |
| 5,837,546 A | 11/1998 | Allen et al. |
| 5,972,199 A | 10/1999 | Heller et al. |
| 5,989,921 A | 11/1999 | Charlton et al. |
| 6,294,281 B1 | 9/2001 | Heller |
| 6,475,661 B1 | 11/2002 | Pellegri et al. |
| 6,475,805 B1 | 11/2002 | Charm et al. |
| 6,500,571 B2 | 12/2002 | Liberatore et al. |
| 6,531,239 B2 | 3/2003 | Heller |
| 6,713,308 B1 | 3/2004 | Lu et al. |
| 6,844,200 B2 | 1/2005 | Brock |
| 7,018,735 B2 | 3/2006 | Heller |
| 7,045,342 B2 | 5/2006 | Nazareth et al. |
| 7,144,742 B2 | 12/2006 | Boehringer et al. |
| 7,160,637 B2 | 1/2007 | Chiao et al. |
| 7,226,442 B2 | 6/2007 | Sheppard, Jr. et al. |
| 7,236,821 B2 | 6/2007 | Cates et al. |

(Continued)

FOREIGN PATENT DOCUMENTS

| | | |
|---|---|---|
| GB | 1 357 494 | 6/1974 |
| WO | WO 98/35053 | 8/1998 |

OTHER PUBLICATIONS

Boitieux et al. "Oxygen electrode-based enzyme immunoassay for the amperometric determination of hepatitis B surface antigen", Analytica Chimica Acta, 1984, 309-313.*
Zhang et al. "Detection of~103 copies of DNA by an electrochemical enzyme-amplified sandwich assay with ambient O2 as the substrate", Anal. Chem. 2004, 76:4093-4097.*
Wilson et al. "Paramagnetic bead based anzyme electrochemiluminescence immunoassay for TNT", J of Electroanalytical Chemistry, 2003, 557:109-118.*
Dill et al. "Multiplexed analyte and oligonucleotide detection on microarrays using several redox enzymes in conjunction with electrochemical detection" Lab Chip, 2006, 6:1052-1055.*

(Continued)

*Primary Examiner* — Bin Shen
(74) *Attorney, Agent, or Firm* — The Kelber Law Group; Steven B. Kelber

(57) ABSTRACT

An assay system is provided of great sensitivity and portability where the presence of a specific target in a sample, as well as its concentration (qualification and quantification) is detected by reason of a potential or voltage in a closed circuit, built up a redox reaction. The reaction is produced by binding a capture moiety to an enzymatic redox reaction partner, allowing the capture moiety to bind to any target in the sample, and washing any such bound target. The bound target, if not immobilized, may be immobilized through use of a second capture moiety. Substrate for the enzyme is then added. The action of the enzyme upon the substrate frees electrons, creating a potential across an anode and cathode which may be separated by a membrane.

3 Claims, 9 Drawing Sheets

Specification includes a Sequence Listing.

(56) References Cited

U.S. PATENT DOCUMENTS

| | | | |
|---|---|---|---|
| 7,238,440 | B2 | 7/2007 | Damore et al. |
| 7,238,442 | B2 | 7/2007 | Heller |
| 7,241,266 | B2 | 7/2007 | Zhou et al. |
| 2004/0245101 | A1 | 12/2004 | Winner et al. |

OTHER PUBLICATIONS

Caruana et al. "Enzyme-amplified amperometric detection of hybridization and of a single base pair mutation in an 18-base oligonucleotide on a 7-um-diameter microelectrode", J. Am. Chern. Soc. 1999, 121:769-774.*

Lutkenhaus et al. "Electrochemically enabled polyelectrolyte multilayer devices: from fuel cells to sensors", Soft Matter, 2007, 3:804-816.*

Quero et al. "Health care applications based on mobile phone centric smart sensor network", IEEE, 2007, 6298-6301.*

Definition of amperometric: 1 page.*

Guo et al. "direct electron transfer of glucose oxidase and biosensing of glucose on hollow sphere-nanostrucuted conducting polymer/metal oxide composite", Phys. Chern. Chern. Phys., 2010, 12:12153-12159.*

Katz, E. et al., "A Biofuel Cell Based on Two Immiscible Solvents and Glucose Oxidase and Microperoxidase-11 monolayer-functionalized electrodes", *New J. Chem.*, pp. 481-487 (1999).

Katz, E et al., "A non-compartmentalized glucose I O2 biofuel cell by bioengineered electrode surfaces", *Journal of Electroanalytical Chemistry*, vol. 479, pp. 64-68 (1999).

Palmore, G. et al., "Electro-enzymatic reduction of dioxygen to water in the cathode compartment of a biofuel cell", *Journal of Electroanalytical Chemistry*, vol. 464, pp. 110-117 (1999).

Palmore, G. et al., "A methanol / dioxygen biofuel cell that uses NAD+-dependent dehydrogenases as catalysts: application of an electro-enzymatic method to regenerate nicotinamide adenine dinucleotide at low overpotentials", *Journal of Electroanalytical Chemistry*, vol. 443, pp. 155-161 (1998).

Trudeau, F. et al., "Reagentless Mediated Laccase Electrode for the Detection of Enzyme Modulators", *Analytical. Chemistry.*, vol. 69, No. 5, pp. 882-886 (Mar. 1, 1997).

Winner, I. et al., "A biofuel cell based on pyrroloquinoline quinone and microperoxidase-111 monolayer-functionalized electrodes", *Bioelectrochemistry and Bioenergetics*, vol. 44, pp. 209-214 (Jan. 1998).

Winner, I. et al., "Biofuel cell based on glucose oxidase and microperoxidase-11 monolayer-functionalized electrodes", *J. Chem. Soc., Perkin Trans 2*, vol. 8, pp. 1817-1822 (Aug. 1998).

Galhaup C., et al., Enhanced formation of laccase activity by the white-rot fungus Trametes pubescens in the presence of copper, *Appl. Microbiolog Biotechno*l, 56: pp. 225-232 (2001).

Galhaup C., et al., "Characterization of the major laccase isoenzyme from Trametes pubescens and regulation of its synthesis by metal ions" *Microbiology*, 148: 2159-2169 (2002).

Gorbatova ON., et al., *Priki Biokhim Mikrobiol*. 36(3): pp. 272-277 (May-Jun. 2000) English Abstract provided.

Katz et al., "Biochemical fuel cells", *Handbook of Fuel Cells—Fundamentals, Technology and Applications*, vol. 1, Chapter 21, pp. 1-27 (2003).

Leitner C., et al., "Purification and Characterization of a laccase from the white-rot fungus Trametes multicolor" *Appied Biochemistry and Biotechnology*, vols. 98-100: pp. 497-507 (2002).

Palmore, G. et al., "Microbial and Enzymatic Biofuel Cells". *American Chemical Society*, Enzymatic Conversion of Biomass for Fuels Production, Chapter 14, pp. 271-290 (1994).

European Search Report dated May 23, 2011, received in Application No. 08832734.1.

Stoellner, et al., "Membrane-immobilized Haptoglobin as Affinity Matrix for a Hemoglobin A1C Immunosensor", Analytica Chimica Acta 470 (2002) 111-119.

Weetall, et al., "A Simple Inexpensive Disposable Electrochemical Sensor for Clinical and Immuno-Assay", Biosensors 3 (1987/88) 57-63.

Ogasawara, et al., "Electrochemical Microdevice with Separable Electrode and Antibody Chips for Simultaneous Detection...", Biosensors and Bioelectronics 21(2006) 1784-1790.

* cited by examiner

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: second complexing ("SC") oligonucleotide
      #100003_15_amino (5'-NH2 modified 15 nucleotides)

<400> SEQUENCE: 1
aggatgacac ctaga                                                    15

<210> SEQ ID NO 2
<211> LENGTH: 36
<212> TYPE: DNA
<213> ORGANISM: Artificial Sequence
<220> FEATURE:
<223> OTHER INFORMATION: first complexing ("FC") oligonucleotide
      #100003_19_polyA (36 nucleotides)

<400> SEQUENCE: 2
gtgatcggga gtgtgtccaa aaaaaaaaaa aaaaaa                             36

<210> SEQ ID NO 3
<211> LENGTH: 39
<212> TYPE: DNA
<213> ORGANISM: Artificial Sequence
<220> FEATURE:
<223> OTHER INFORMATION: target specific ("TS") olignucleotide 100003_39
      (39 nucleotides)
```

```
<400> SEQUENCE: 3
tggacacact cccgatcacc acgatctagg tgtcatcct                                39
```

SELF-ACTUATING SIGNAL PRODUCING DETECTION DEVICES AND METHODS

PRIORITY DATA AND INCORPORATION BY REFERENCE

This application claims benefit of priority to U.S. Provisional Patent Application No. 60/960,112, filed Sep. 17, 2007 and U.S. Provisional Patent Application No. 61/123,280, filed Apr. 7, 2008 which are incorporated by reference in its entirety. This application is related to a patent application filed on even date herewith naming the same inventors, U.S. application Ser. No. 12/212,007, filed Sep. 17, 2008.

BACKGROUND OF THE INVENTION

Field of the Invention

In the following discussion certain subject matter will be described for background and introductory purposes. Nothing contained herein is to be construed as an "admission" of prior art. Applicant expressly reserves the right to demonstrate, should it be deemed necessary and where appropriate, that any subject matter referenced herein does not constitute prior art under the applicable statutory provisions of Title 35 of the United States Code.

The present invention relates to novel devices and methods for analyte detection. The embodiments are useful in a wide range of fields, including, inter alia, in vitro diagnostics, clinical medicine, developmental medicine, pharmaceuticals, pharmacogenomics, homeland security, military/defense, agro-chemical, industrial chemical, cosmetics, dietary supplements, genomics, toxicology, metabolomics, therapeutics, emergency response, holistic medicine, homeopathy, genetic screening, and general product quality assurance.

There continues to be an increased need and demand for new and improved detection methodologies that exhibit, for example, one or more of the following characteristics: (i) accurate, (ii) highly selective (i.e., capable of correctly discriminating between possible target molecules with low background and false results—positive or negative), (iii) high sensitivity (iv) rapid results, (v) readily adapted to targets of interest, (vi) cost effective and, optionally, (vii) capable of portable (i.e., field) use. The present invention addresses each of these demands and fulfills a long-felt and unfulfilled need in detection technology. In addition to the general demand for accurate, reliable and sensitive testing methods and devices, recent quality issues in pharmaceutical and health care related products produced in China highlight the need for improved quality assurance diagnostics. The present invention satisfies, inter alia, each of these criteria.

By way of background, the following discussion of various technologies is provided to aid in understanding the context in which the present invention was developed. The headings are not intended to be delimiting, inclusive or exclusive of any particular subject matter, but instead are employed simply to aid the reader in a contextual manner.

Related Art

This invention pertains to materials, devices, systems and methods for the detection of target substances in a larger volume. The volume, or sample, may be liquid or dry, but it is placed ultimately in a liquid test environment. The invention disclosed and claimed herein is particularly suited to the detection of targets present in extremely small concentrations, whose detection is nonetheless essential. The detection of various targets such as antibodies, spores, bacteria and the like, at an initial and low concentration, may permit the implementation of preventive or treatment strategies not available if detection is deferred until a later time. This invention has its background in a variety of established detection assays and reagents, discussed below.

BACKGROUND OF THE TECHNOLOGY

ELISA Methods

Enzyme-linked immunosorbent assay (ELISA) is a widely used method for measuring the concentration of a particular molecule (e.g., a hormone or drug) in a fluid such as serum or urine. ELISA assays were first described by Engvall and Perlman in 1971. ELISA assays have been and continue to be widely used, despite the numerous disadvantages and deficiencies that are exhibited thereby. An example of a commonly used ELISA-type assay are the so-called home pregnancy tests, which by way of example, typically consist of a handheld plastic housing, a sorbent material impregnated with one or more reagents including a calorimetric enzyme system. Urine is applied to the device directly, and the liquid travels along the sorbent material in what has come to be known as a "lateral flow" configuration. See, e.g. U.S. Pat. Nos. 4,703,017, 4,855,240, 5,356,785, 5,468,648, 5,656,503, 5,766,961, 5,837,546, 5,989,921, 6,475,805, 6,713,308, 6,844,200, 7,045,342, 7,144,742, each of which is incorporated by reference in their entirety. The target analyte (e.g., human chorionic gonadotropin (HCG) in the case of a pregnancy test), is detected by antibodies that have been generated "against" that target; that is, for which it is the antigen. Antibodies function to immobilize the target analyte—if present—and in turn, the enzyme-linked calorimetric system. A polyclonal antibody, will recognize and bind to more than one epitope. Monoclonal antibodies are often used in such immunoassay applications. A monoclonal antibody is designed to only recognize, i.e., react or bind to one specific antigenic determinant, or epitope. Due to the diversity found in the immune system and the production of monoclonal antibodies from immortalized cells of the immune system, first described by Kohler and Milstein in 1975 (Kohler & Milstein, 1975), antibodies can be raised against a huge number of different antigens by standard immunological techniques. Potentially any agent can be recognized by a specific antibody that will not react with any other agent.

ELISA is often employed in the laboratory by coating a vessel, such as a microtiter plate with an antibody specific for a particular antigen to be detected, e.g., a virus or bacteria, adding the sample suspected of containing the particular antigen or agent, allowing the antibody to bind the antigen and then adding at least one other antibody, specific to another region of the same agent to be detected. This use of two antibodies can be referred to as a "sandwich" ELISA. It is common that, the second antibody or even a third antibody is used that is labeled with a chromogenic or fluorogenic reporter molecule to aid in detection. The procedure can comprise the use of a chemical substrate which is required by an antibody conjugated enzyme to produce a visual signal.

Among the various disadvantages, the need for multiple antibodies, which do not cross-react with other agents, and the incubation steps involved mean that it is difficult to detect more than a single agent in a sample in a short time period. Additionally, the ability to multiplex (i.e., simultaneously attempting to detect multiple agents in one sample) is limited by the number of labels that can be attached to the antibodies and therefore used to differentiate between the different agents. Sensitivity concerns arise from the ability to generate quality antibodies and having sufficient levels of the target analyte to yield an accurate and reproducible sample. For example, in the use of a pregnancy test, a negative test does not mean the individual is not pregnant, and indeed, it is recommended that the individual repeat the test over a period of weeks to allow the HCG levels to reach the threshold of detection of the ELISA test.

Nucleic Acid Detection Methods

Another commonly used method of detection is focused on the detection of the presence of and/or characterization of nucleic acids. Several methods of detecting nucleic acids are available including various PCR and hybridization techniques.

PCR (the polymerase chain reaction) is well known in the art and is described, for example, in U.S. Pat. Nos. 4,683,195 and 4,683,202 to Mullis and Mullis et al., respectively. PCR is used for the amplification and detection of low levels of specific nucleic acid sequences. PCR can be used to for the purpose of increasing low concentrations of a target nucleic acid sequence in an effort to achieve a more readily detectable level. In general terms, PCR involves introducing an excess of two oligonucleotide primers, which are complementary to the sequence on the two strands of a desired double-stranded target sequence. The sample suspected of containing the target sequence is heated and/or otherwise treated to denature any double-stranded DNA sequences present in the sample, followed by cooling in the present of the oligonucleotide primers to allow primer hybridization. Following hybridization, the primers are extended with a polymerase so as to form complementary strands. The steps of denaturation, hybridization, and polymerase extension can be repeated as often as needed, in order to obtain relatively high concentrations of a segment of the desired target sequence. A variant of this technique is the ligase chain reaction, or LCR, which uses polynucleotides that are ligated together during each cycle. Other variants exist, but none have been as widely accepted as PCR. PCR requires laboratory conditions and equipment and highly trained personnel. It is not suited for field use, and is only applicable to nucleic acid targets. PCR often suffers from non-specific amplification of non-target sequences.

Nucleic acid hybridization techniques commonly involve detecting the hybridization of two or more nucleic acid molecules. Such detection can be achieved in a variety of ways, including labeling the nucleic acid molecules and observing the signal generated from such a label. Traditional methods of hybridization, including, for example, Northern and Southern blotting, were developed with the use of radioactive labels which are not amenable to automation. Radioactive labels have been largely replaced by fluorescent labels in most hybridization techniques. Representative forms of other hybridization techniques include, for example, the "cycling probe reaction", branched DNA methodologies, the Invader™ Assay (Third Wave Technologies, Inc; Madison Wis.), and Hybrid Capture™ (Digene Corporation; Gaithersburg, Md.).

In general, fluorescence-based detection systems all suffer from the problem of background cause by incident, ambient or other light source.

Additionally, nucleic acid detection techniques, are restricted in use to the detection of nucleic acids. Therefore, agents such as proteins, drugs, hormones, chemical toxins, and prions, which do not contain nucleic acids, cannot be detected by these nucleic acid hybridization techniques.

Biosensors

A biosensor can be defined generally as an analytical device incorporating biological and chemical sensing elements, integrated with circuitry suitable to enable the conversion of a biological interaction into an electronic signal. A representative example of a biosensor, are the glucose monitoring devices commonly used in diabetes care.

Biosensors comprise a diverse variety of mechanisms and forms. A relatively common, but not universal, feature of biosensors is the use of enzymes. In such biosensors, typical configurations involve the use of an enzyme system in association with two electrodes that are separated by a membrane barrier, which enzyme system is specific for the target which is intended to be detected (e.g., glucose oxidase for the detection of glucose) and whereby the enzyme-substrate interaction provides an analytical means to detect the enzyme's substrate.

Radio Frequency Identification (RFID)

Radio Frequency Identification (RFID) is an identification method that relies, in part, on storing and remotely retrieving data using devices commonly referred to as RFID tags (or transponders). RFID systems typically consist of a number of components including tags, handheld or stationary readers, data input units, and system software. RFID provides an automated (or automatable) way to collect information about a product, place, time or transaction quickly, easily and without certain elements of human error. RFID provides a contact-less data link, without requiring line-of-sight and relatively immune to harsh or dirty environments that restrict other automatic ID technologies such as bar codes. In addition, RFID can provide more than just an identification device. An RFID tag can be used as a data carrier, and information can be written to and updated on the tag in real time.

Commonly used RFID tags come in a variety of shapes, sizes and read ranges, typically configured in a manner/form that can be attached to, incorporated into, or otherwise associated with a product, animal, or person for the purpose of tracking and identification. Representative tags including thin and flexible "smart labels" which can be laminated between paper or plastic, chip-based RFID tags containing silicon chips and, often some form of antenna with is capable of receiving and/or transmitting radio waves. So-called passive RFID tags require no internal power source, instead deriving their power source from a radio wave transmitted from a "reader." So-called active RFID tags require an internal power source. Tags can also be "semi-active"—relying upon both internal and external power sources for their proper functioning.

RFID has been applied to a variety of applications in varied industries. Today, RFID is used for such applications as vehicle and facility access control, automotive security (e.g., anti-theft) systems, product and asset tracking, and supply chain automation. Additional applications include payment and loyalty management, sports timing, pet and livestock identification, authentication and document management. U.S. Pat. No. 7,241,266, discloses a biosensor device that employs a form of RFID technology, which RFID is powered by electro-active polymer generator embedded in muscle tissue for generating power.

A Few Relevant Terms/Concepts Relating to RFID Include:

Active tag. An RFID tag that contains a battery and a transmitter to send information to an RFID reader, rather than reflecting a signal back to the reader from a tag (as a passive tag does).

Agile reader. An RFID reader that can read tags operating at different frequencies or different communication protocols.

Air interface protocol. The standards that govern how RFID tags and readers communicate.

Anti-collision. Anti-collision algorithms are used to collect data from multiple RFID tags at the same time from the same RFID reader without interference.

Backscatter. The communication method between a passive RFID tag and a reader. An RF signal sent by a reader is reflected back to the reader from the tag, which is modulated to transmit data.

Beacon. An active or semi-passive RFID tag that is programmed to "wake up" and broadcast a signal at pre-set intervals.

Concentrator. A device used to gather data from multiple RFID readers at the same time.

Inductive coupling. A RFID reader antenna and a tag antenna each have a coil, which together form a magnetic field. The RFID tag draws electrical energy from this field, which powers its microchip. The microchip then changes the electrical characteristics of the tag antenna. These changes are sensed up by the reader antenna and converted into a serial number for the RFID tag.

Interrogator. Another name for an RFID reader.

Passive tag. An RFID tag without a power source or transmitter. Radio waves from an RFID reader are collected from the RFID tag antenna, which powers up the microchip in the tag. The tag is then able to send back information stored in the chip to the reader.

Resonant Capacitor.

RFID reader. A device used to communicate with RFID tags. The reader has one or more antennas, which emit radio waves and receive signals back from the tag. The reader is also sometimes called an interrogator because it "interrogates" the tag.

RFID tag. A microchip attached to an antenna in a package. An RFID tag contains a unique serial number at a minimum, but commonly contain other information about a product. RFID tags can be passive, semi-passive or active.

Semi-passive/Semi-active tags. Similar to active RFID tags, but the battery is typically used only to power the RFID chip—not to broadcast a signal to a reader.

Transponder. A radio-frequency transmitter-receiver combo. Another term for a RFID tag.

Fuel Cells

The term "fuel cells" typically refers to systems that seek to utilize catalysts for the conversion of chemical energy into electrical energy. Many organic substrates undergo combustion in oxygen or are oxidized with the release of energy. Methanol, ethanol and glucose, for example, are abundant raw materials and, as such, can be attractive candidates for fuel cell reactions.

The general concept of a fuel cell involves the siphoning of electrons from the catalytic reaction through the use of redox moieties. For example, in a fuel cell employing methanol as the fuel source, the oxidation of methanol at the anode can be represented by:

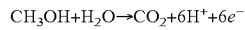

$$CH_3OH + H_2O \rightarrow CO_2 + 6H^+ + 6e^-$$

and the reduction of oxygen at the cathode can be represented by:

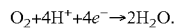

$$O_2 + 4H^+ + 4e^- \rightarrow 2H_2O.$$

Thus, the combined reactions proceed with an "excess" of two electrons. If one can harness the excess electrons, that energy can be used for other purposes, including, inter alia, to create a battery.

A subset of the general class of fuel cells, are so-called "biofuel cells" i.e., fuel cell sytems that rely upon biocatalysts (e.g., enzymes). (See, e.g., Katz et al., "Biochemical fuel cells", Handbook of Fuel Cells—Fundamentals, Technology and Applications, 1, Ch. 21 (2003); Katz, E. et al., "A Biofuel Cell Based on Two Immiscible Solvents and Glucose Oxidase and Microperoxidase-I I monolayer-functionalized electrodes", New J. Chem., pp. 481-487 (1999); Katz, E. et al., "A non-compartmentalized glucose I $O_2$ biofuel cell by bioengineered electrode surfaces", Journal of Electroanalytical Chemistry, vol. 479, pp. 64-68 (1999); Palmore, G. et al., "Microbial and Enzymatic Biofuel Cells". Enzymatic Conversion of Biomass for Fuels Production, Ch. 14, pp. 271-290 (1994); Palmore, G. et al., "A methanol/dioxygen biofuel cell that uses $NAD^+$-dependent dehydrogenases as catalysts: application of an electro-enzymatic method to regenerate nicotinamide adenine dinucleotide at low overpotentials", Journal of Electroanalytical Chemistry, vol. 443, pp. 155-161 (Feb. 10, 1998); Palmore, G. et al., "Electroenzymatic reduction of dioxygen to water in the cathode compartment of a biofuel cell", Journal of Electroanalytical Chemistry, vol. 464, pp. 110-117 (1999); Trudeau, F. et al., "Reagentless Mediated Laccase Electrode for the Detection of Enzyme Modulators", Anal. Chem., vol. 69, No. 5, pp. 882-886 (Mar. 1, 1997); Willner, I. et al., "A biofuel cell based on pyrroloquinoline quinone and microperoxidase-I I monolayer-functionalized electrodes", Bioelectrochemistry and Bioenergetics, vol. 44, pp. 209-214 (Jan. 1998); Willner, I. et al., "Biofuel cell based on glucose oxidase and microperoxidase-I I monolayer-functionalized electrodes", J. Chem. Soc., Perkin Trans 2., vol. 8, pp. 1817-1822 (Aug. 1998); U.S. Pat. Nos. 4,581,336; 4,578,323, 4,126,934 and 3,941,135; United States Patent Appl. No: 20040245101, each of which is incorporated by reference). Recent advances in various biological systems have been announced, including the preparation of a biofuel cell battery that runs on glucose, fruit juice, soda, etc. See, e.g., www.slu.edu/x14605.xml. Biofuel cells commonly include a redox-based reaction that includes electrodes separated by one or more membranes. See, e.g., U.S. Pat. Nos. 5,660,940, 6,500,571, 6,475,661. Examples of membrane-less fuel cell applications have also been reported. See, e.g., U.S. Pat. No. 7,238,440.

The use of "fuel cell" methods in conjunction with biosensors or implantable devices recently have been reported. However, the applicability of these fuel cells is limited due to, inter alia, issues of practicality (lack thereof), low sensitivity, ineffectiveness, strict reliance on the enzymatic substrate for detection and other problems (see, e.g., 7,226,442, 7,236,821, 7,160,637, 7,018,735), each of which are overcome by the devices and methods of the present invention.

Biological/Diagnostic Detection Assays

Biological assays typically involve relatively complex systems that include a large numbers of compounds, thus current screening assays can be expensive and time-consuming. In certain assays, radioactive labeling of reference compounds have been used; however, these assays are expensive and require complicated disposal protocols and dedicated laboratory areas due to the use of radioactive materials. In other screening assays, fluorescently-labeled materials have been used, but such assays often suffer from the occurrence of false positives, difficulty in detection of the fluorescent signal, high background, unacceptable signal-to-noise rations, and the denaturation of the fluorescent compound(s) during handling and/or storage. In still other assays, calorimetric detection has been employed. Such calorimetric assays tend to suffer from the same or similar drawbacks as the fluorescence-based assays. Each of these prior methods are subject to the limited number of unique identifiers available for identification, given the fact that only a limited number of different radioactive labels and fluorescent compounds are commercially available.

Mentioned supra, the lateral flow type devices are a common format for such biological assays/diagnostic devices. See, e.g. U.S. Pat. Nos. 4,703,017, 4,855,240, 5,356,785, 5,468,648, 5,656,503, 5,766,961, 5,837,546, 5,989,921, 6,475,805, 6,713,308, 6,844,200, 7,045,342, 7,144,742, each of which is incorporated by reference in their entirety.

An ideal detection assay would combine the versatility and selectivity of antibody recognition, speed, accuracy, sensitivity, broad applicability, the ability to multiplex and, optionally, the ability to perform such assays in "field applications" (e.g., outside of the confines of research, analytical or clinical laboratories), and/or without the need for external power supplies or instrumentation, all while overcoming the inherent deficiencies exhibited by currently known detection methods.

The present invention satisfies each of these objectives and fulfills one or more long-felt and unfulfilled needs in the field of detection technology.

SUMMARY OF THE INVENTION

The present invention provides, inter alia, detection devices and methods that exhibit increased sensitivity, are high selectivity, and can perform measurements in a rapid fashion while exhibiting little or no background. The present invention also provides embodiments of such devices and methods that are, optionally, suitable for and/or capable of functioning in "field applications" (e.g., outside of the confines of research, analytical or clinical laboratories), and/or without the need for external power supplies or instrumentation. Devices and methods for detecting one or more target agents are taught.

There exists an ever increasing demand for accurate, sensitive, and rapid biological/chemical analysis and/or assays (a subset of which are commonly referred to as "diagnostic assays"). The need for rapidity is clearly secondary to that of accuracy, sensitivity, ease of use and applicability to the particular task. The present invention provides, inter alia, detection devices and methods that exhibit increased sensitivity, high selectivity, and/or reduced background over the prior art devices and methods. The present invention also provides embodiments of such devices and methods that are, optionally, suitable for and/or capable of functioning in "field applications" (e.g., outside of the confines of research, analytical or clinical laboratories), and/or without the need for external power supplies or instrumentation. Devices and methods for detecting one or more target agents are taught.

Embodiments of the present invention are drawn to self-actuating signal-producing ("SASP") detection devices and methods that are capable of providing accurate and rapid biological and chemical analysis and diagnostic assays (collectively referred to herein as "SASP diagnostic devices and methods"). It should be understood that this term is intended to be broadly construed to include all analytic and diagnostic assays in all applicable fields of use including, inter alia, continuous monitoring of biological and disease states, in vitro diagnostics, food assays/diagnostics, cosmetic applications, agro-chemical applications, industrial chemical applications, defense related applications, homeland security related applications, etc.

It is an object of the present invention to provide SASP devices and methods that are not able to generate a signal in the absence of a target analyte.

It is an object of the present invention to provide SASP devices and methods that have high sensitivity.

It is an object of the present invention to provide SASP devices and methods that have low background and low incidence of false positives.

It is an object of the present invention to provide SASP devices and methods that have low thresholds of detection.

It is an object of the present invention to provide SASP devices and methods that have high selectivity.

Preferred embodiments of the present invention include SASP devices and methods, wherein part or all the energy needed to generate said signal is created, directly or indirectly, by a biocatalytic reaction. In certain preferred embodiments, said signal is indicative of the selective binding of a target analyte in, for example, a diagnostic assay. Said signals include, inter alia, RF signals (including, but not limited to, RFID), electrical signals, photo-electronic signals, photo-reactive signals and light emission. In those embodiments where said RF is generated from an RFID circuit, said RFID's can be passive, active or semi-active types.

Of particular significance, the embodiments of the present invention are not limited to an catalytic system that utilizes the desired target analyte as the substrate. Said another way, the biocatalytic reagents (e.g., enzymes, enzyme/redox systems, and the like) of the preferred embodiments do not use the target analyte(s) for the generation of energy. Prior art biocatalytic diagnostic devices have focused on enzyme systems that utilize the target analyte as the substrate (e.g., glucose oxidase and/or glucose dehydrogenase for glucose detection and/or monitoring). In marked contrast, the enzyme systems of the preferred embodiments of the present invention are preferably "unrelated" to the target analyte, and in preferred embodiments, is unable to utilize the target analyte as a substrate. This aspect of the present invention provides several significant and non-limiting advantages which include, inter alia: (1) a "universal" format assay can be developed irrespective of the target analyte, thereby reducing manufacturing costs, quality control costs, optimization time, etc., (2) applications for target analytes for which enzyme and/or redox systems are not known, readily available or which do not exist, (3) the ability to utilize optimized enzyme systems for a wide array of analytes, and (4) the ability to develop detection methods and systems that rely upon low cost, readily available and/or relatively abundant fuel substrates.

The devices and methods of the present invention include, inter alia, solution phase, flow through, capillary flow, and lateral flow formats. It is important to recognize that the underlying methodology(ies) is/are not limited to any particular flow format or mechanism, but instead are adaptable to most analytic methodologies.

In certain preferred embodiments, the SASP devices and methods include instrumentation, so called "chips" (consumables), and methods for using same in automated, semi-automated and/or manual testing instrument devices. In addition, preferred embodiments include "portable" SASP devices and methods (i.e., embodiments that are suitable for field applications, including, inter alia, embodiments that do not require an instrument to run the assay/analysis). Such portable embodiments are particularly suitable for field use where electrical power is not available, not practical, impossible, or hampered by other impediment, and in particular, where accuracy, sensitivity, specificity and rapid testing is required outside of a controlled or relatively controlled (e.g., laboratory) environment. Such portable embodiments are highly beneficial in contexts including, inter alia, battlefield, conflict zones, emergency response teams, Homeland Security, rural areas, isolated areas (e.g., camping situation employing water safety testing assay), under-developed countries, disaster zones (e.g., earthquake, hurricane, etc.) and the like.

In preferred embodiments, the catalytic system is associated, directly or preferably indirectly, with one or both electrodes of a fuel cell type device. The electrodes of said device can be associated, directly or indirectly, with a circuit (e.g., an RF generating circuit), whereby electrons generated by said catalytic system are in communication with said circuit. Said communication can be by conductive, inductive, wireless transmission or other transmissible means.

In certain preferred embodiments, one or more enzymes of said catalytic system are associated with said electrode(s) by way of a selective chemical association. Said chemical association can be one of more of, inter alia, nucleic acid moiety(ies), antibody moiety(ies), ligand moiety(ies) or the like.

In a preferred embodiment, an RF signal is created by the selective binding of a target analyte in the presence of the SASP device, thereby creating a source of electrons capable of powering an RF (e.g., RFID) circuit. In certain preferred embodiments, said selective binding occurs in conjunction with lateral flow molecular association.

In implantable embodiments, the device can be preferably localized subcutaneously and can, for example, utilize physiological solutions to generate signal, thereby providing a method for detecting the presence of and/or monitoring the level of specific molecules (e.g., glucose, metabolites, hormones, proteins, etc.).

In certain embodiments, the SASP detection devices and methods are capable of real time monitoring of the levels (e.g., concentration) of a desired target, through, inter alia, the measurement of the electronic signal and/or RF pulse frequency generated by the enzyme system employed. For example, the concentration of the target analyte will, in certain embodiments, be directly proportional to the concentration of enzyme system localized at the detection circuitry. Thus, in the case of an RFID-based device and/or method, the pulse frequency (i.e, the rate at which the RFID circuit is charged and discharges its RF signal) can indicate the concentration of the target analyte. In preferred embodiments, a standardized reference/control circuit is employed, thereby enabling the accurate quantification of the target analyte.

In certain preferred embodiments, the SASP detection devices and methods include the ability to generate, inter alia, one or more of (i) RF signals (including, but not limited to, RFID), (ii) electrical signals, (iii) photo-electronic signals, (iv) photo-reactive signals and (v) light emission, without the use of an external power source. Instead, these embodiments of the SASP devices and methods are capable of providing a signal thru the generation of electron flow derived from a catalytic reaction, and preferably a biocatalytic reaction and more preferably a biocatalytic reaction in conjunction with an associated redox reaction. In certain preferred embodiments the redox reactions include an associated biocatalyst. In certain preferred embodiments, one or more electron mediator moieties are employed in the SASP detection device and/or method.

In certain preferred embodiments, the target analyte(s) in a sample are selectively "captured" by a capture moiety associated with an electrode and/or electrode-like device, which electrode and/or electrode-like device is in communication, directly or indirectly, with an electronic circuit, preferably wherein said circuit provides a means by which the presence of the target can be determined, directly or indirectly, thru the generation of an electronic signal.

A further objective of the present invention are SASP detection devices and methods that are highly specific with respect to the desired target and signaling related thereto. The present invention provides high specificity both with respect to the chemical/biological specificity imparted by their intrinsic design, and is further enhanced by the fact that the SASP devices and methods are inherently not subject to interference by contaminants.

A further objective of the present invention are SASP detection devices and methods that comprise enzyme/redox systems that present the low electrical power output. An advantage of such low power output systems includes, inter alia, the reduction or elimination of redox transformation of contaminants at the electrode, thereby increasing selective signaling.

The SASP detection devices and methods of the present invention are particularly suited for use in areas, locations, circumstances where it is either impractical or not possible to utilize devices requiring external power sources.

An object of the invention is to provide an enzyme electrode system for use in liquid mixtures of components for detecting the presence of, measuring the amount of and/or monitoring the level of one or more selected components capable of undergoing an enzyme-catalyzed reaction, in which an oxido-reductase enzyme associated with, preferably in an immobilized state, a surface of an electron collector, preferably the electrode(s) of an RF circuit capable of being employed in a SASP detection device/method.

A further objective is to provide a handheld detector for use in conjunction with the SASP detection devices and methods of the present invention.

The embodiments of the present invention satisfy at least one or more of the forgoing objectives, embodiments, characteristics and/or features. The present invention is not limited to the description provided within the Summary, but instead does include other embodiments, specific and/or general aspects and/or specific or general features of the invention that are described in other portions of the specification. The objectives, advantages, aspects, embodiments and/or features of the foregoing Summary as well as other objects, embodiments, advantages, aspects and features of the invention will become apparent to those persons skilled in the art upon reading the specification, claims and figures.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

So that the general manner in which the features, advantages and objects of the present invention are attained/attainable and can be understood in detail, a more particular description of the invention, briefly summarized above, may be had by reference to the embodiments that are illustrated in the appended drawings. It is to be noted, however, that the appended drawings illustrate only certain embodiments of this invention and are therefore not to be considered limiting of the scope of the present invention, for the present invention may admit to and expressly includes, other embodiments not illustrated herein.

DETAILED DESCRIPTION OF THE INVENTION

This invention is described below generically and by specific example. The examples are not intended to be limiting, and do not identify limits of the invention unless specifically recited in the claims appended hereto. By the same token, the invention is described in the context of the drawings and figures described above. The figures are representative only, intended to provide the reader with specific and fine scale description of the sweeping scope of the invention. Unless so indicated by recitation in the following claims, the invention is not limited to any embodiment or device so illustrated.

MODE(S) FOR CARRYING OUT THE INVENTION

The various embodiments will be described in detail with reference to the accompanying drawings. Wherever possible, the same reference numbers will be used throughout the drawings to refer to the same or like parts. As indicated above, this invention relies, in preferred embodiments, on the chemical reaction between and enzyme and its substrate. A typical redox pair, discussed below, is glucose oxidase and its substrate, glucose. There are a variety of ways to describe the chemical reaction that occurs between the redox enzyme and its substrate. The enzyme remains intact, but in acting upon the substrate, it typically generates electrons and "digests" or "degrades" or removes some chemical moiety from the substrate. This term is referred to herein as "acting upon." Thus, when the enzyme contacts the substrate and alters it, in the process of generating electrons or electric potential, it is described herein as an event where the enzyme "acts upon" the substrate.

DETAILED DESCRIPTION OF CERTAIN PREFERRED EMBODIMENTS OF THE INVENTION

Brief Overview By Schematic

Although the invention of this patent application takes its from in a variety of specific embodiments, it can be generally characterized by reference to basic common elements. The invention employs a redox pair of reagents which liberate electrons, to provide a detectable signal when a circuit is completed. In broad outline, one of the reagents is typically an enzyme which is present only if the target is present. It is combined with the substrate for that enzyme. A variety of enzyme/substrate pairs can be used, but in general, an oxidase or dehydrogenase is used. Thus, glucose can be used with glucose oxidase or glucose dehydrogenase, lactose with lactose oxidase or dehydrogenase, etc.

Figure 1:
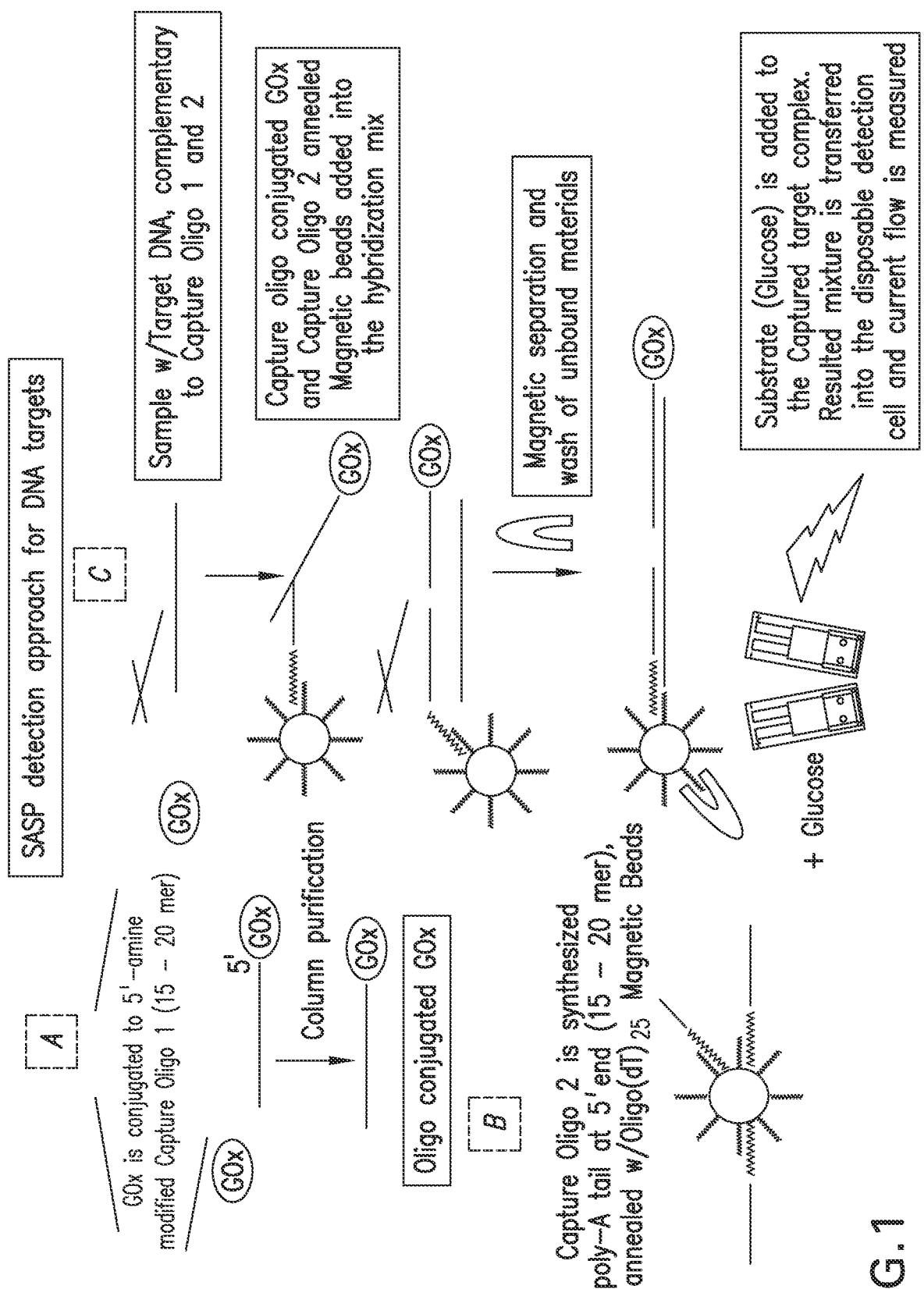
FIG. 1 is a schematic illustration of the application of this invention to detect DNA targets, such as DNA encoding a particular protein of interest.

Referring to FIG. 1 of this application, in broad outline, the assay system, methods and devices of this invention can be used to detect a wide variety of targets. One popular target is DNA of a specific sequence, or primary structure. This sequence determines what role the DNA plays, and if it encodes a protein, the identity and role of that protein. Thus, detection of target DNA is a common and important aspect of this invention. In the practice of this invention, because the detection of a signal generated by very few DNA moieties is at the heart of the invention, suppression of background noise is essential. IN the schematic of FIG. 1, background noise is reduced in part by selection of the treated agents with a magnet, the agents being repeatedly washed after being isolated. Other capture methodologies will occur to those of skill in the art, including those referenced above.

As shown, in the first or "A" stage of the invention, a member of a redox reaction pair, preferably an oxidase or dehydrogenase, is employed as a charge or electricity generation agent in the presence of the target. In the particular embodiment of the schematic, and generally, a preferred embodiment, glucose oxidase (GOx) is employed. This catalyst is coupled or conjugated to a "capture oligomer" or "Capture Oligo." The capture oligo has a sequence that will hybridize, under appropriate conditions known to those of skill in the art, to one portion of the target DNA. The conjugated GOx is purified against a column, to provide one essential reactant of the system.

A second reactant or reagent for the system of the invention is prepared in the second or B step of the method of use of the invention. This is a second capture oligomer, one which binds to a part of the target, through hybridization, which is distinct from the portion or sequence to which the first capture oligomer binds too. This second capture oligomer is in turn bound to a magnetic bead through conventional methods known to those of skill in the art. The second capture oligomer is collected by a magnet, and washed to purification.

The third or reaction step of the invention calls for combining the two capture oligomers with the sample. These may be added simultaneously, or sequentially, depending on the desires of the practitioner. Where the capture oligomers bind the target at the same hybridization conditions, and do not otherwise compete for, or interfere with each other, in hybridizing with any target present, it may be convenient to add them together. When added to the sample under hybridization conditions, if there is any target in the sample, the target will be bound by the oligomer which presents, in this case, glucose oxidase, and the oligomer which is bound to a magnetic bead. The magnetic bead provides a simple method for purification. A magnet is applied to the vessel which holds the hybridization mixture, which may be a test tube, an ampoule, a microarray plate well, etc. The material is washed (×3). Any target bound by the second capture oligomer will be retained by the applied magnetic field.

The washed captured target is then added to a small volume loaded with the substrate for the redox catalyst, in this case, glucose. The presence of the target insures the presence of GOx, which reacts with the glucose to free electrons. Thus, the strength of signal obtained (the electricity flowing through the circuit created) is directly related to the amount of target present (each GOx molecule is tied to one target moiety). Qualification, confirming the presence of minute amounts of the target, and quantification, determining the amount of target present by the strength of the signal, can both be achieved. In absolute terms, given a 1:1 signal to target ratio (greater rations can be achieved using the turnover of the enzyme or multiple signaling moieties per molecule of target) threshold detection of 100 attomoles of target/1-3 pM concentration is well within the capabilities of the invention.

Figure 2:
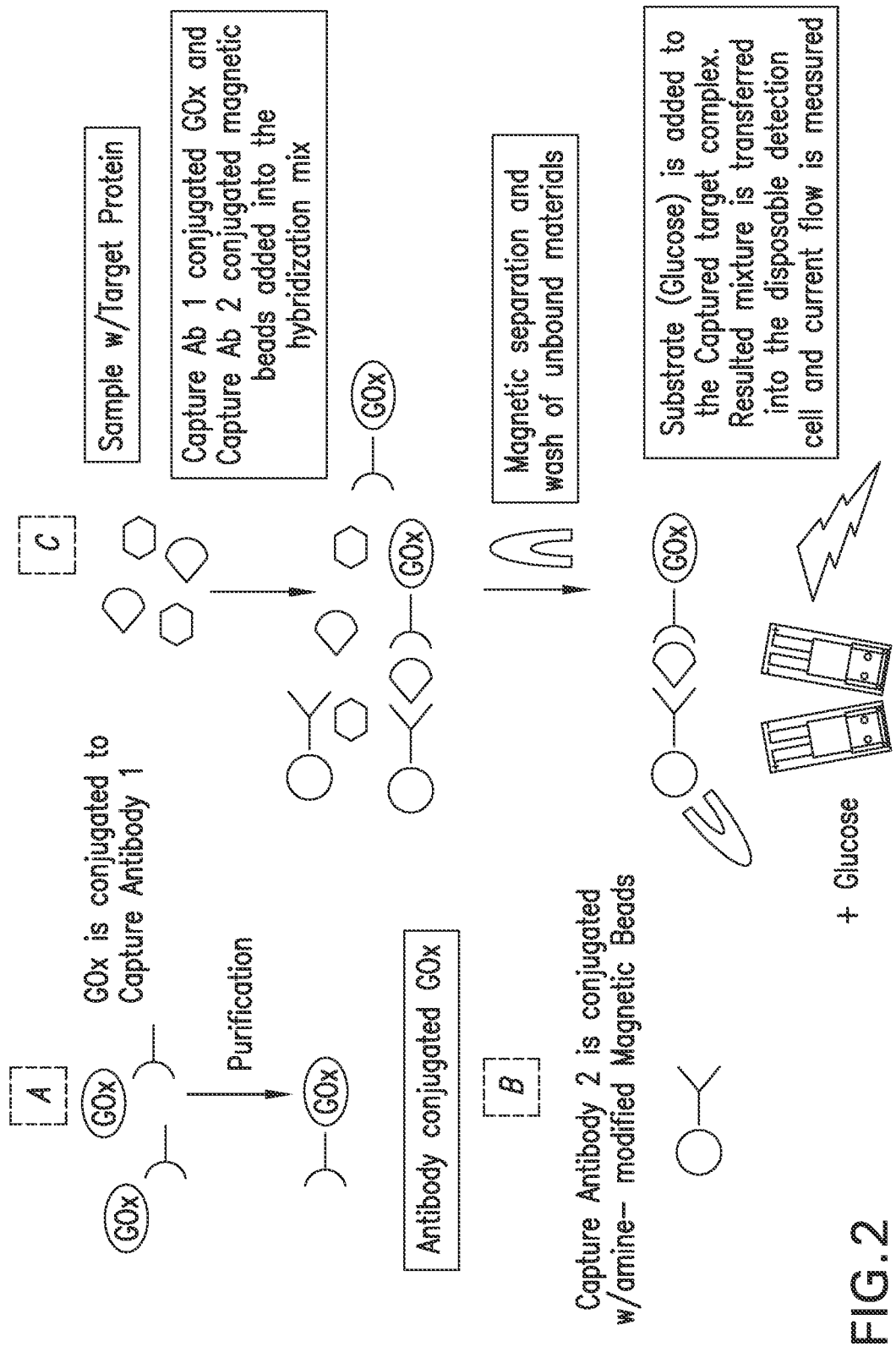
FIG. 2 is a schematic illustration of the application of this invention to detect protein targets, such as a particular protein expressed by a microorganism of interest.

Similar to the method of detecting the presence of a target DNA, as shown in FIG. 2, proteins are similarly detected. Rather than using the hybridization capabilities of DNA, use can be made of a different kind of binding moiety, antibodies. As discussed above, antibodies can be raised against a specific target—that is, they bind to that target preferentially. In the practice of the invention, the redox partner, again in this example, glucose oxidase, is conjugated to an antibody specific for the target of interest. Following conventional purification, this first capture antibody reagent is prepared.

As with the DNA target, a second capture reagent is employed. Instead of an oligomer, a second antibody is used. The antibody is conjugated to a magnetic bead in this embodiment. As before, the magnetic bead makes purification, both before and after binding to the target, easier, suppressing background noise. Other purification methods are known to those of skill in the art. The second stage or "Step B' of this process involves purification of the second capture antibody.

The $1^{st}$ and second capture antibodies bind to different portions of the target—different epitopes, to avoid competition or interference in binding. The two capture antibodies are combined, simultaneously or sequentially, with the sample. Any target present in the sample will be bound by both the $1^{st}$ capture antibody, and its given epitope, which is conjugated with a GOx moiety, and the $2^{nd}$ capture antibody, bound to a magnetic bead, and binding the target at its given epitope. The resulting antibody-target-antibody complex is separated from the detection sample by application of a magnet, which draws off any target present, the rest of the sample being washed away.

The enzyme substrate, in this case glucose, is added to the material separated off. Target bound by the antibody bound to the magnetic bead bears a glucose oxidase conjugated to the $1^{st}$ capture antibody. Addition of glucose drives the reaction, liberating electrons and driving the detectable signal. To distinguish the signal from a null signal (background) it may be desirable to delay closing the circuit for a few measurement cycles, say one to five minutes. This builds up a potential which, when the circuit is closed, provided a sudden strong signal which is equal to a signal obtained by constant measurement from the beginning. The "spike" of the delayed measurement is equal to the area under the curve of the constant measurement.

The above descriptions are directed to the situation of a homogenous phase, or liquid assay, that requires separation of the target from the remainder of the sample. In another preferred embodiment, the SASP technology of the present invention is used for in situ detection of target materials. For example, the redox enzyme is conjugated to a moiety such as an oligomer or antibody that is capable of selectively binding with a target specie within the sample (e.g., a tissue biopsy sample) to be tested. The sample is them placed into an appropriate detection chamber, preferably a one chambered reaction chamber wherein the cathode is painted with or otherwise separated from the anode by an appropriate polymeric membrane (i.e., Nafthion). The sample and foregoing conjugate and substrate are contacted within the reaction chamber and tested for the presence of the target material as in the preceeding examples. Similarly, the presence of the target in the heterogenous sample may be the key inquiry (is there any target present). In these embodiments, a single capture moiety is used—the first capture moiety, bearing or conjugated with the redox enzyme. The second capture moiety, used to separate bound target, is not necessary.

The present invention is drawn to novel SASP detection devices and methods are capable of providing accurate and rapid biological and chemical detection, analysis and diagnostic assays (collectively referred to herein as "SASP detection devices and methods"). It should be understood that the term "SASP detection devices and methods" is intended to be broadly construed to include detection, analysis and diagnostics assays in all applicable fields of use including, inter alia, in vitro diagnostic, clinical medicine, developmental medicine, pharmaceutical, pharmacogenomics, homeland security, defense, agro-chemical, industrial chemical, cosmetic, dietary supplement, genomics, toxicology, metabolomics, therapeutics, emergency response, holistic medicine, homeopathy, genetic screening, and general product quality assurance applications.

The SASP detection devices and methods of the present invention include the ability to generate, inter alia, one or more types of signals including, but not limited to: (i) RF signals (including, but not limited to, RFID), (ii) electrical signals, (iii) photo-electronic signals, (iv) photo-reactive signals and/or (v) light emission. In preferred embodiments, the SASP devices/methods are capable of generating said signal(s) without the need for an external power source to provide all of the power necessary for signaling. In preferred embodiments, the SASP detection devices and methods of the present invention are capable of providing a signal thru the generation of electron flow derived from a catalyst, more preferred a biocatalyst and more preferred one or more of the foregoing used in conjunction and/or otherwise associated with a redox and/or redox-type reaction. In certain preferred embodiments the redox reactions include an associated biocatalyst. In certain preferred embodiments, one or more electron mediator moieties are associated with the redox reaction and/or the biocatalyst.

The SASP detection devices and methods of the present invention comprise one or more electronic circuits, which circuits are capable of generating a signal as described herein, thru, inter alia, the transfer of electrons from a catalytic reaction, preferably a biocatalytic reaction including, inter alia, an enzymatic redox system, to said circuit(s). In certain preferred embodiments, the electronic circuit is capable of generating a RF signal, and more preferably, an RFID signal. In those embodiments comprising RFID circuitry, said RF circuits can be of the passive, active and/or semi-active type, where some or all of the electrical source provided is that generated through, inter alia, a catalytic and/or redox reaction.

In certain embodiments, the enzymatic and/or redox reaction, is capable of directly charging the resonant capacitor of an RFID circuit, thereby providing the power required for RFID signal production.

In certain embodiments, the enzymatic and/or redox electron potential can supplement a provided power source such as a battery or similar means. In other embodiments, the enzymatic and/or redox electron potential is capable of powering a circuit, such as a switch, FET or the like; thus, the energy created by the SASP device and/or method, provides an electronic signal to an RFID circuit/device, which RFID device can then signal by system generated and/or traditional powering means (e.g., RF, induction, battery, external power supply, etc.). These types of embodiments are preferred in those applications wherein the target analyte is present in low concentration—thus, the provided power source is capable of generating a portion of the electronic potential required for a signaling event, but not sufficient energy (either inherently insufficient and/or controlled (e.g., by resistance)) to generate the signal. In such embodiments, a lower degree (e.g., concentration) of target binding is thereby capable of generating the electron potential required for a signaling event.

The SASP detection devices and methods of the present invention can be employed in the determination of the presence, concentration and/or the identity of chemical and/or biological target analytes in situ and in samples of, strictly by way of non-limiting example, environmental, industrial, or clinical origin (e.g. biological samples, blood tests, biopsies, genetic materials, etc.). The SASP detection devices and methods of the present invention are suited to and intended for use in a wide range of detection/assay applications, including, inter alia, infectious disease, glucose monitoring, genetic testing, cancer testing, water testing, impurity screening and validation, cosmetics, fermentation processes, emergency response (e.g., toxic spills, accidents, contamination, terrorist acts, chemical/biological warfare), and the like. The SASP detection devices and methods of the present invention are capable of selective detection of most analytes including, inter alia, nucleic acids, proteins, and/or small molecules (e.g., toxins, drugs, metabolites, starting materials, contaminants, etc.).

The SASP detection devices and methods are highly specific both with respect to the chemical/biological specificity imparted by their intrinsic design, and is further enhanced by the fact that the SASP devices and methods are inherently not subject to interference by contaminants.

In accordance with certain preferred embodiments, a system for the determination of, inter alia, the presence, concentration and/or identity of a target analyte contained in a liquid medium, comprises a SASP detection device/method and a detector capable of determining the presence of, inter alia, (i) RF signals (including, but not limited to, RFID), (ii) electrical signals (e.g., voltage and/or current), (iii) photo-electronic signals, (iv) photo-reactive signals and/or (v) light emission, without the use of an external power source. In preferred embodiments said signal is generated by said SASP detection device/method, directly or indirectly, via an electron transfer reaction. The devices and methods of the present invention are not limited to electron transfer reactions wherein the target analyte is being oxidized or reduced and, as such, are widely applicable and, among other details, are significantly improved over existing methodologies and sensor devices.

In certain preferred embodiments, the SASP detection devices/methods comprise one or more catalyst systems capable of undergoing a catalytic oxidation and/or reduction. In certain preferred embodiments the enzyme and/or redox system comprises one or more electrodes, and more preferably, one anode and one cathode. In certain preferred embodiments, one or both electrodes are associated, directly or indirectly, with one or more catalysts (e.g. one or more enzymes) and/or redox moieties. Said catalysts can be immobilized on one or more electrode(s) and/or otherwise associated therewith (e.g., proximally associated, solution phase, etc.), wherein, for example in the case of an enzyme, said enzyme is associated with one of the electrodes can catalyze an oxidation or reduction reaction in which a substrate is oxidized or reduced and, preferably, is capable of transferring one or more electrons from said reaction to an electron transfer partner capable of catalyzing a reaction in which the oxidizer is oxidized and/or the reducer is reduced, respectively; in the presence of the substrate.

The anode and/or cathode employed in certain preferred embodiments of the present invention can have a variety of shapes, forms and structures and be made from a variety of materials. For example, the anode and/or cathode can be formed as plates, mesh, wires, tubes, or other shapes of conductive material. (See, e.g., U.S. Pat. No. 7,238,442, incorporated herein by reference). The anode and/or cathode can also be a conductive film formed over a base material. Said conductive films can be formed on said base material by a variety of methods, including, for example, sputtering, physical vapor deposition, plasma deposition, chemical vapor deposition, screen printing, and other coating methods.

The anode and/or cathode employed in certain preferred embodiments of the present invention can be formed using a conductive material, such as, for example, metal, carbon, conductive polymer, or metallic compound. Suitable conductive materials are typically non-corroding and can include, for example, gold, vitreous carbon, graphite, platinum, ruthenium dioxide, and palladium, as well as other materials known to those skilled in the art. Suitable non-conducting base materials for use with a conductive film include plastic and polymeric materials, such as, for example, polyethylene, polypropylene, polyurethanes, and polyesters. It will be understood that the anode and cathode of any particular embodiment are not necessarily made using the same materials.

The conductive material and/or the optional non-conducting base material can be, for example, non-porous, porous or microporous. For example, the conductive material and/or the optional non-conducting base material may be formed, for example, as a mesh, a reticulated structure (e.g., reticulated graphite), a microporous film, or a film that is permeable to the anode reductant and/or cathode oxidant. The surface area of the electrode can also be increased by roughening or other texturing. Preferably, the actual exposed surface area of the anode and/or cathode is larger than the macroscopic geometric surface area because the anode and/or cathode are reticulated, mesh, roughened, porous, microporous, and/or fibrous. In addition, the conductive material and/or the optional non-conducting base material can be and/or include, ion selective membrane.

Suitable electrodes can be comprised of, for example, one or more conducting and/or semi-conducting materials including, for example gold, platinum, palladium, silver, carbon, copper, indium tin oxide (ITO), and the like. For invasive analyses the electrodes are preferably constructed of bio-compatible and non-toxic materials/substances. For certain embodiments, graphite paste is a preferred material due to ease of fabrication and sufficiently large surface area. In certain embodiments, the association of the enzyme with the electrodes may be accomplished by mixing, for example, graphite powder, siloxane-ferrocene polymer and glucose oxidase and blending the resultant mixture into a paste which is subsequently packed into a well at the base of an electrode housing or applied to the electrode base plate surface. Exemplary carbon-based electrodes are discussed in U.S. Pat. No. 4,970,145, incorporated herein by reference.

The SASP detection devices and methods of the invention are preferably used without a membrane between the electrodes, thereby providing a significant benefit and ease of use and design. Less preferred embodiments can employ, as required for the particular configuration, one or more membrane and/or membrane-like materials.

The catalyst(s)/enzyme(s) associated with the electrode(s) of the preferred embodiments are preferably, but not necessarily, of a redox type, and preferably redox enzymes. It is important to recognize that some redox enzymes are dependent on co-factors such as for example: flavin adenine dinucleotide phosphate (FAD), pyrroloquinoline quinone (PQQ), nicotinamide adenine dinucleotide ($NAD^+$), nicotinamide adenine dinucleotide phosphate ($NADP^+$), hemes, iron-sulfur clusters and others, however, the presence of or reliance upon a co-factor is not required by the present invention. In those embodiments where such co-factors are required and/or beneficial, the system preferably comprises such co-factors.

In certain preferred embodiments, SASP detection devices/methods comprise (a) a cathode that is configured and/or oriented in a manner so that it is capable of electro-reducing oxygen and (b) an anode that is configured and/or oriented in a manner so that it is capable of electro-oxidizing hydrogen, alcohols (e.g., methanol), carbohydrates (e.g., glucose), carboxylic acids (e.g., formic acid) or carboxylic esters (e.g., methyl formate).

In certain embodiments it is preferable that the system comprise one or more electrolytes. Where such electrolytes are employed, the electrolytes can be selected from, inter alia, those commonly used in redox reactions such as, inter alia, batteries, fuel cells, biofuel cells, etc. In general terms, the electrolytes in a system such as that employed in certain embodiments of the present invention, for example, where protons are generated on the anode, to expedite transportation of those protons to the cathode where reaction with an oxidant takes place. In a membrane containing fuel cell, a proton exchange membrane commonly serves to separate the anode from the cathode and can, optionally, serve to conduct protons from one electrode to the other. In a membrane-free fuel cell, electrolytes typically facilitate the movement of protons to the requisite electrode. Examples of electrolytes suitable for use in embodiments of the present invention, include, but are not limited to: salts, acids and bases. The electrolytes can be introduced and/or present in the form of dissolved salts, acids, or bases or, for example, may be introduced and/or present in the form of polymeric salts, acids or bases. Preferred embodiments include systems where the electrolytes, for example salts, are also capable of functioning as a buffer. Examples include, but are not limited to, those salts containing phosphates, citrates and acetates. Especially preferred are salt buffers in the pH range of about 2-7.

In certain embodiments, the function of the catalyst(s)/redox moiety(ies) comprise the catalysis of an electrochemical reaction of an anode reductant or cathode oxidant. Preferred redox catalysts may be comprised of species capable of reversibly transferring electrons, including (but not limited to) enzymes and organometallic redox complexes. Preferred redox catalysts are enzymes.

Representative examples of suitable enzymes include, but are not limited to glucose oxidase (GOx), lactate dehydrogenase (LDH), fructose dehydrogenase, choline oxidase, alcohol dehydrogenase, amino acid oxidase, cytochromes, etc.

There are a variety of enzymes that are useful in association with the cathode including, for example: laccase and cytochrome C oxidase for electro-reduction of oxygen; and, peroxidases for electro-reduction of hydrogen peroxide. Similarly, useful enzymes on the anode include: hydrogenases for the electro-oxidation of hydrogen; oxidases and dehydrogenases for electrooxidation of methanol, other alcohols, glucose, lactate and other substrates; alcohol oxidase, formaldehyde dehydrogenase and formate dehydrogenase for electrooxidation of methanol; pyranose oxidase for electro-oxidation of D-glucose, L-sorbose and D-xylose; and, glucose oxidase, oligosaccharide dehydrogenase and pyrroloquinoline quinone (PQQ) glucose dehydrogenase for electro-oxidation of glucose. A non-limiting list of enzymes useful in the present invention is given in U.S. Pat. No. 6,294,281, hereby incorporated by reference.

More preferred enzymes for use in the present invention are those enzymes selected from the oxido-reductase group, a group containing (but not limited to): laccase, ascorbate oxidase, cytochrome c oxidase, multi-copper oxidases, bilirubin oxidase, blue copper oxidases, alcohol oxidase, formaldehyde dehydrogenase and formate dehydrogenase, L-lactate dehydrogenase, malate dehydrogenase, glucose oxidase, microbial pyruvate oxidase, and catechol oxidase. Laccases are more preferred at the cathode in certain embodiments of the invention herein.

In general, laccase (polyphenol-oxidase [EC 1.10.3.2]) is a multicopper oxidase that couples the one-electron oxidation of four substrate molecules to the four-electron reduction of dioxygen to water. Thus, laccase is useful for the biocatalytic reduction of dioxygen to water in the SASP detection devices and methods. Several genes that encode different isoforms of laccase have been isolated and sequenced (e.g. *Trametes versicolor, T. pubescens, Coriolus hirsutus* and *Pleurotus ostreatus*); and, much work has been performed to biochemically characterize these enzymes (Galhaup C., et al., *Microbiology*, 2002 July; 148(Pt 7):2159-2169; Leitner C., et al., *Appl Biochem Biotechnol.* 2002 Spring; 98-100:497-507; Galhaup C., et al., *Appl Microbiol Biotechnol.* 2001 July; 56(1-2):225-232; Gorbatova O. N., et al., *Prikl Biokhim Mikrobiol.* 2000 May-June; 36(3):272-277).

The substrates utilized in the present invention are those capable to undergo catalytic oxidation or reduction reactions. Preferably, the substrate is usually an organic substance. Examples of representative substrates include, inter alia, sugar molecules (e.g. glucose, fructose, sucrose, mannose, etc); hydroxy or carboxy compounds (e.g. lactate, ethanol, methanol, formic acid, etc.), ATP, carbon sources, nitrogen sources, phosphorous sources, sulfur sources, amino acids, or any other organic materials that serve are capable of functioning as a substrate for redox reactions, and more preferably, redox type enzymes.

It is particularly preferred that the enzyme systems are chosen according to the ability to oxidize a substrate which exhibits one or more of the following characteristics: (i) readily available, (ii) readily subjected to the intended redox reaction, and (iii) capable of yielding a surplus of electrons for the SASP device and/or method from said redox reaction.

In certain embodiments, the preferred enzymes are non-oxygen-specific flavo-protein or quino-protein enzymes, in particular glucose oxidase and glucose dehydrogenase. Other flavo-protein enzymes include aldehyde oxidase (aldehydes), glycolate oxidase (glycolate), glutathione reductase (AND(P)H), lactate oxidase (lactate), L-amino acid oxidase (L-amino acids), lipoamide dehydrogenase (NADH), pyruvate oxidase (pyruvate), sarcosine oxidase (sarcosine), choline oxidase (choline) and xanthine oxidase (xanthine), where the substrate to which the enzyme is specific has been denoted in parenthesis.

In other embodiments, the preferred enzymes are quino-protein enzymes such as, for example, methylamine dehydrogenase (methylamine) and methanol dehydrogenase (methanol and other alcohols).

In other embodiments, the preferred enzymes are heme-containing enzymes which can be oxidized by ferrocenes such as, for example, horse-radish peroxidase (hydrogen peroxide), lactate dehydrogenase (lactate) and yeast cytochrome C peroxidase (hydrogen peroxide).

In other embodiments, the preferred enzymes are cupro-protein enzymes such as, for example, galactose oxidase (galactose) and the metalloflavin protein enzyme carbon monoxide oxidoreductase (carbon monoxide).

Also, the enzyme can be derived from thermophilic organisms, thereby increasing enzyme stability over time and storage. In those embodiments where thermophile enzymes are employed, the reaction can optionally be conducted at high temperature. By the operation at high temperature, a diffusion rate-determining step is accelerated, so that larger sensitivity and output can be obtained.

Enzymes from thermophilic organisms are commonly referred to as thermostable enzymes. Representative examples of thermostable enzyme include laccase from the thermophilic fungus *Myceliophthora thermophilia*, cytochrome C perioxidases from thermophilic bacterium PS3 and *Thermus thermophilus*, peroxidase from soybean, and pyranose oxidase from the white rot fungus *Phlebiopsis gigantea*. Other commercially available thermostable enzymes include L-lactate dehydrogenase from *Bacillus*, malate dehydrogenase from *Thermus* species, glucose oxidase from *Aspergillus*, microbial pyruvate oxidase, and urate oxidase from *bacillus*. Thermostable enzymes that hydrolyze larger biological molecules into electrooxidizable sugars include, for example, α-amylase from *Bacillus stearothermophilus*, β-amylase from *aspergillus*, glucan-1,4-α-glucosidase from *Rhizopus niveus*, cellulase from *Aspergillus niger*, endo-1-3(4)-β-glucanase from *Aspergillus niger*, dextranase from *Leuconostoc mesenteroides*, α-glucosidase from *Bacillus stearothermophilus*, β-glucosidase from *Caldocellum saccharolyticum*, β-galactosidase from *aspergillus*, β-fructofuranosilidase from yeast, and lactase from *Aspergillus oryzae*.

In addition, whether or not the enzyme is inherently thermostable, the preferred enzyme can be immobilized in a non-conducting inorganic or organic polymeric matrix to increase the thermostability of the enzyme. Discussion regarding immobilization of an enzyme in an inorganic polymeric matrix is found in U.S. Pat. No. 5,972,199, and PCT Publication WO 98/35053, each of which is incorporated herein by reference. A sol-gel polymerization process provides a method for the preparation of an inorganic polymeric matrix (e.g., glass) by the polymerization of suitable monomers at or near room-temperature. Suitable monomers include, for example, alkoxides and esters of metallic and semiconducting elements, with preferred metallic and semiconducting elements including Si, Al, Ti, Zr, and P. Such preferred monomers include silicon and have a silicon to oxygen ratio from about 1:2 to about 1:4.

For example, enzymes can be immobilized in silica polymeric matrices made by sol-gel processes, such as the hydrolysis of tetramethoxysilane or another polyalkoxysilane that contains one or more silicon atoms. Condensation of the resulting silanol in the presence of the enzyme results in entrapment of the enzyme. This process has been referred to as sol-gel immobilization. Binding of enzymes in silica or other inorganic polymeric matrices formed from sol-gels can stabilize the enzyme. Entrapment of glucose oxidase, a glycoprotein, in a silica sol-gel matrix greatly improves the stability of the enzyme, which retains activity when heated in water to 98° C. for 10 minutes.

An enzyme stabilized by the silica sol gel matrix can be ground to a fine powder and dispersed in a silicone, preferably in an elastomeric silicone, and most preferably in a water-based elastomeric silicone precursor. This dispersion is then applied to the cathode as a binder of the enzyme. The binder preferably includes material to extract and store oxygen from the environment. Silicone is a preferred binder in this layer due to its ability to dissolve oxygen and its oxygen permeability. Elastomeric silicones are preferred because of high oxygen solubility.

The stability of an enzyme in an inorganic polymeric matrix depends, at least in part, on the ionic characteristics of the enzyme and those of the immobilizing, often inorganic, polymeric matrix. A hydrated silica gel has an isoelectric point (pI) (i.e., the pH at which the net charge on the molecule is zero) near pH 5. It has been demonstrated that glucose oxidase, with pI=3.8, retains its activity upon sol-gel immobilization and is stabilized when immobilized in the hydrated silica gel matrix so that the half-life of the enzyme can be increased by about 200-fold at 63° C., Lactate oxidase (pI=4.6) and glycolate oxidase (pI ≈9.6), on the other hand, each lost at least 70% of their activity upon immobilization in a hydrated silica gel and the stability of these two enzymes was not greatly improved.

In contrast to the loss of activity of these enzymes in hydrated silica alone, it has been shown that when poly(1-vinyl imidazole) (PVI) (a weak base) or poly(ethyleneimine) (PEI) (a stronger base) was used to form an adduct in the hydrated silica gel, the half-life of lactate oxidase (pI=4.6) increased more than 100-fold at 63° C. and the enzyme was immobilized without significant loss of activity. The adduct can be formed by, for example dissolving lactate oxidase in an aqueous buffer solution in which poly(1-vinyl imidazole) is co-dissolved, and the lactate oxidase-poly(1-vinyl imidazole) mixture is immobilized in silica by the sol-gel process, a stable, immobilized lactate oxidase is obtained. The stabilized lactate oxidase can be heated in water to 90° C. for 10 minutes and still retain enzymatic activity. A similar adduct which retains enzymatic activity can be formed with poly(ethyleneimine).

It is thought that functionally essential, positively charged surface residues (e.g., arginine) of the lactate and glycolate oxidases may interact with negatively charged polysilicate anions of the hydrated silica, resulting in a decrease in activity upon sol-gel immobilization. However, when the enzyme surface is enveloped by a flexible polycation buffer (i.e., PVI and/or PEI, depending on the isoelectric point of the enzyme) then the polysilicate anions can interact with the cationic buffer molecules, and not with the cationic residues of the enzyme, thereby stabilizing the enzyme by encasement in the silica gel. Thus, it is thought that PVI and PEI form adducts, acting as polycationic buffers for enzymes such as lactate oxidase. PEI also acts as a cationic buffer for enzymes such as glycolate oxidase. It is thought that PVI is a less preferred buffer for glycolate oxidase, likely due to the fact that glycolate oxidase is a stronger base.

In general, the addition of a polycation, such as, for example, poly(1-vinyl imidazole) or poly(ethyleneimine), prior to sol-gel immobilization stabilizes the enzyme. Preferably, the added polycation is a more basic polyelectrolyte than the enzyme. Enzymes with high isoelectric points often need more basic polyelectrolytes for stabilization. Poly (ethyleneimine) is more basic than poly(1-vinyl imidazole).

Poly(1-vinyl imidazole), a polycation at pH 7, can bind at this pH to enzymes such as lactate oxidase, that are polyanions at pH 7. Thus, the addition of a particular polymer to a particular enzyme can increase the stability the enzyme. In the case of lactate oxidase, addition of poly(ethyleneimine), also a polybasic polymer and also multiply protonated at pH 7, in place of poly(1-vinyl imidazole) can improve stability of the enzyme, although not as much as the addition of the preferred polymer, poly(1-vinyl imidazole). Such stabilized enzyme can typically be used at higher temperatures and/or for longer durations than would be possible if the enzyme were immobilized alone in a sol-gel.

Sol gel matrices in which an enzyme is immobilized and stabilized are often not electron conductors. This type of matrix, however, can be modified by binding, often through covalent bonds, a redox functional group to the matrix or its precursor. Examples of suitable redox functional groups include, inter alia, the redox species described above for use in the redox polymer, including, for example, osmium, ruthenium, and cobalt complexes having ligands including one or more pyridine and/or imidazole rings. Moreover, the redox functional group of such constructs can preferably include a spacer arm covalently or coordinatively attached a metal cation of the redox functional group or one of the ligands. One end of the spacer arm is covalently linked to, for example, silicon atoms of the matrix. The other end of the spacer arm is covalently or coordinatively linked to the redox functional group. The enzyme can be immobilized in such a matrix and electrons can be exchanged between the enzyme and the electrode using the redox functional group coupled to the matrix.

In some embodiments, non-corroding, electron-conducting particles are disposed within the matrix to increase the conductivity of the matrix; particularly, for those matrices that include attached redox functional groups. Examples of such particles include graphite, carbon black, gold, and ruthenium dioxide. Typically, these particles have a diameter of 1 .mu.m or less and a surface area of 1 $m^2/g$ or more, preferably, 10 $m^2/g$ or more, and, more preferably, 100 $m^2/g$ or more. Alternatively, $VOCl_3$ can be hydrolyzed to form a polymeric matrix, that, when reduced, is conducting.

In other embodiments, an enzyme is immobilized and stabilized in a sol gel matrix and the enzyme catalyzes a reaction of a chemical to form a product that is subsequently electrooxidized or electroreduced in the presence of a second enzyme that is electrically coupled to an electrode. For example, glucose can react in the presence of glucose oxidase that is stabilized in a sol gel matrix to form gluconolactone and hydrogen peroxide. The hydrogen peroxide diffuses out of the sol gel matrix to the proximity of the cathode and is electroreduced to water by a thermostable enzyme, such as soybean peroxidase.

Water, which is typically the primary mass transporting medium in many biological systems, is an electrical insulator. Although the solubility of many compounds is high in water, these compounds cannot be electrolyzed in the absence of transport of electrons through the aqueous medium. This can be accomplished by a variety of methods, including, for example, using a redox polymer, and in particular a redox hydrogel. Redox polymers generally provide for adequate transport of electrons if the redox polymer includes active redox functional groups that are mobile and can carry electrons between the analyte and the electrode. For example, a redox hydrogel typically contains a large amount of water. Water soluble reactants and products often permeate through the redox hydrogel nearly as fast as they diffuse through water. Electron conduction in the redox hydrogel is through electron exchange between polymer segments that are mobile after the polymer is hydrated.

In certain preferred embodiments, an anode redox polymer and/or cathode redox polymer are deposited on the anode and cathode, respectively. In general, the redox polymers comprise electroreducible and electrooxidizable ions, functionalities, species, or other molecules and/or moieties having redox potentials. Preferably, these redox potentials are well-defined. The redox potentials of the redox hydrogels are typically within a range at which water is neither electrooxidized or electroreduced. At neutral pH and 25° C., this range is from about (−)0.65 V to about (+)0.58 V versus the standard calomel electrode (SCE) (i.e., from about (−)0.42 V to about (+)0.81 V versus the standard hydrogen electrode (SHE)). A preferred range of the redox potential for the anode redox polymer is from about −0.65 V to about +0.05 V (SCE). A preferred range of the redox potential for the cathode redox polymer is from about +0.3 V to about +0.7 V (SCE).

In some embodiments, the preferred redox polymers include a redox species bound to a polymer which can in turn be immobilized on the working electrode. In general, redox polymers suitable for use in the invention have structures or charges that prevent or substantially reduce the diffusional loss of the redox species during the period of time that the sample is being analyzed. The bond between the redox species and the polymer may be covalent, coordinative, or ionic. Examples of useful redox polymers and methods for producing them are described in U.S. Pat. Nos. 5,262,035; 5,262,305; 5,320,725; 5,264,104; 5,264,105; 5,356,786; 5,593,852; and 5,665,222, incorporated herein by reference. Although any organic or organometallic redox species can be bound to a polymer and used as a redox polymer, preferred redox species include a transition metal compound or complex. In such embodiments, preferred transition metal compounds or complexes include osmium, ruthenium, iron, and cobalt compounds or complexes. In the preferred complexes, the transition metal is coordinatively bound to one or more ligands and covalently bound to at least one other ligand. The ligands are often mono-, di-, tri-, or tetradentate. The more preferred ligands are heterocyclic nitrogen compounds, such as, for example, pyridine and/or imidazole derivatives. For example, the multidentate ligands typically include multiple pyridine and/or imidazole rings. Alternatively, polymer-bound metallocene derivatives, such as, for example, ferrocene, can be used. An example of this type of redox polymer is poly(vinylferrocene) or a derivative of poly(vinylferrocene) functionalized to increase swelling of the redox polymer in water.

Another type of redox polymer contains an ionically-bound redox species. Typically, this type of mediator includes a charged polymer coupled to an oppositely charged redox species. Examples of this type of redox polymer include a negatively charged polymer such as Nafion® (DuPont) coupled to multiple positively charged redox species such as an osmium or ruthenium polypyridyl cations. Another example of an ionically-bound mediator is a positively charged polymer such as quaternized poly(4-vinyl pyridine) or poly(1-vinyl imidazole) coupled to a negatively charged redox species such as ferricyanide or ferrocyanide. The preferred ionically-bound redox species is a multiply charged, often polyanionic, redox species bound within an oppositely charged polymer.

A variety of methods may be used to immobilize a redox polymer on an electrode surface and the embodiments of the present invention are not limited to any particular method, expressly identified herein or otherwise know to those of skill in the art. One representative method is adsorptive immobilization. This method is particularly useful for redox polymers with relatively high molecular weights. The molecular weight of a polymer may be increased, for example, by cross-linking. The polymer of the redox polymer may contain functional groups, such as, for example, hydrazide, amine, alcohol, heterocyclic nitrogen, vinyl, allyl, and carboxylic acid groups, that can be crosslinked using a crosslinking agent. These functional groups may be provided on the polymer or one or more of the copolymers. Alternatively or additionally, the functional groups may be added by a reaction, such as, for example, quaternization. One example is the quaternization of PVP with bromoethylamine groups.

Alternatively, the enzyme is immobilized in a non-conducting inorganic or organic polymeric matrix to increase the thermostablity of the enzyme. Discussion regarding immobilization of an enzyme in an inorganic polymeric matrix is found U.S. Pat. No. 5,972,199 and PCT Publication WO 98/35053, each of which is incorporated herein by reference. A sol-gel polymerization process provides a method for the preparation of an inorganic polymeric matrix (e.g., glass) by the polymerization of suitable monomers at or near room-temperature. Suitable monomers can include, for example, alkoxides and esters of metallic and semiconducting elements, with preferred metallic and semiconducting elements including Si, Al, Ti, Zr, and P. The more preferred monomers include silicon and have a silicon to oxygen ratio from about 1:2 to about 1:4.

For example, enzymes can be immobilized in silica polymeric matrices made by sol-gel processes, such as the hydrolysis of tetramethoxysilane or another polyalkoxysilane that contains one or more silicon atoms. Condensation of the resulting silanol in the presence of the enzyme results in entrapment of the enzyme. This process has been referred to as sol-gel immobilization. Binding of enzymes in silica or other inorganic polymeric matrices formed from sol-gels can stabilize the enzyme. Entrapment of glucose oxidase, a glycoprotein, in a silica sol-gel matrix greatly improves the stability of the enzyme, which retains activity when heated in water to 98° C. for 10 minutes.

An enzyme stabilized by a silica sol gel matrix can be ground to a fine powder and dispersed in a silicone, preferably in an elastomeric silicone, and most preferably in a water-based elastomeric silicone precursor. This dispersion is then applied to the cathode as a binder of the enzyme. The binder preferably includes material to extract and store oxygen from the environment. Silicone is a preferred binder in this layer due to its ability to dissolve oxygen and its oxygen permeability. Elastomeric silicones are preferred in this context due to high oxygen solubility.

In certain preferred embodiments, a two enzyme system is employed, said system comprising a first enzyme (E1) to catalyze a reaction for producing a first reaction product (RP1) from a reaction substrate RS1, and a second enzyme (E2) to catalyze a reaction for producing a second reaction product RP2) from a reaction substrate (RS2). In certain preferred embodiments, such enzymes can be chosen for their ability to provide a thermodynamically advantageous electron transfer reaction with low overvoltage from the RS1 to the electrode. It is particularly advantageous to limit the relative distance and an orientation of the E1 and the E2 moeities. In general, without relative positioning, the reaction will be limited by diffusion kinetics—i.e., the time it takes for RP1 produced by the E1 to diffuse to E2 and function as RS2. This typically is a rate-determining step. It is preferred that the enzymes necessary for the electron transfer/generation reactions be oriented is such proximity to maximize the interaction of all necessary reaction components. Preferred methods include tethering the enzymes. Such tethering means are know in the art and include, inter alia, the use of spacer molecules, fusion proteins, complex formation, and the like.

In certain preferred embodiments, the catalyst(s)/enzyme(s) are configured such that that enzyme electrode comprises a conductive base plate, and an enzyme electrically connected with the conductive base plate. In certain embodiments, the enzymes comprise a fusion protein of a first enzyme to catalyze a chemical reaction for producing a first reaction product from a first reaction substrate and a second enzyme to catalyze a chemical reaction for producing a second reaction product from a second substrate, and at least one part of the first reaction product is identical to at least one part of the second reaction substrate.

In certain preferred embodiments of the present invention, the enzyme electrode(s) are associated with the detection portion for detecting a base plate, and in the more preferred embodiment the conductive base plate is in electrical communication, directly or indirectly, with the electronic circuitry of an RF producing circuit, such that the electron flow can provide the power for said circuitry. In certain embodiments, the enzyme electrode with the above-mentioned structure is used as an anode.

In other preferred embodiments, the enzyme electrode where two enzymes are employed, the relative distance between the E1 and the E2 is small, so that the electron transfer reaction from the RS1 of the E1 to the electrode efficiently advances.

In certain preferred embodiments, redox species can be used in conjunction with, or in place of, one or more enzyme catalytic systems. Suitable redox species include, for example, osmium cations complexed with (a) two bidentate ligands, such as 2,2'-bipyridine, 1,10-phenanthroline, or derivatives thereof (the two ligands not necessarily being the same), (b) one tridentate ligand, such as 2,2',2''-terpyridine and 2,6-di(imidazol-2-yl)-pyridine, or (c) one bidentate ligand and one tridentate ligand. Suitable osmium transition metal complexes include, for example, $[(bpy)_2 OsCl]^{+/2+}$, $[(dimet)_2 OsCl]^{+/2+}$, $[(dmo)_2 OsCl]^{+/2+}$, $[terOsCl_2]^{+/2+}$, $[trimetOsCl_2]^{+0/+}$, and $[(ter)(bpy)Os]^{+2/+3}$ where bpy is 2,2'-bypyidine, dimet is 4,4'-dimethyl-2,2'-bipyridine, dmo is 4,4'-dimethoxy-2,2'-bipyridine, ter is 2,2',2''-terpyridine, and trimet is 4,4',4''-timethyl-2,2',2''-terpyridine.

The redox species often exchange electrons rapidly between each other and the electrode so that the complex can be rapidly oxidized and/or reduced. In general, iron complexes are more oxidizing than ruthenium complexes, which, in turn, are more oxidizing than osmium complexes. In addition, the redox potential generally increases with the number of coordinating heterocyclic rings.

Typically, the polymers used for the redox polymers have nitrogen-containing heterocycles, such as pyridine, imidazole, or derivatives thereof for binding as ligands to the redox species. Suitable polymers for complexation with redox species, such as the transition metal complexes, described above, include, for example, polymers and copolymers of poly(1-vinyl imidazole) (referred to as "PVI") and poly(4-vinyl pyridine) (referred to as "PVP"), as well as polymers and copolymer of poly(acrylic acid) or polyacrylamide that have been modified by the addition of pendant nitrogen-containing heterocycles, such as pyridine and imidazole. Modification of poly(acrylic acid) may be performed by reaction of at least a portion of the carboxylic acid functionalities with an aminoalkylpyridine or aminoalkylimidazole, such as 4-ethylaminopyridine, to form amides. Suitable copolymer substituents of PVI, PVP, and poly(acrylic acid) include acrylonitrile, acrylamide, acryihydrazide, and substituted or quaternized N-vinyl imidazole. The copolymers can be random or block copolymers.

The transition metal complexes typically covalently or coordinatively bind with the nitrogen-containing heterocycles (e.g., imidazole and/or pyridine) of the polymer. Alternatively, the transition metal complexes may have vinyl functional groups through which the complexes can be co-polymerized with vinylic heterocycles, amides, nitriles, carboxylic acids, sulfonic acids, or other polar vinylic compounds, particularly, for those compounds whose polymer is known to dissolve or swell in water.

Typically, the ratio of osmium or ruthenium transition metal complex to imidazole and/or pyridine groups ranges from 1:10 to 1:1, preferably from 1:2 to 1:1, and more preferably from 3:4 to 1:1. Generally, the redox potentials of the hydrogels depend, at least in part, on the polymer with the order of redox potentials being poly(acrylic acid) <PVI<PVP.

A variety of methods may be used to immobilize a redox polymer on an electrode surface. One method is adsorptive immobilization. This method is particularly useful for redox polymers with relatively high molecular weights. The molecular weight of a polymer may be increased, for example, by cross-linking. The polymer of the redox polymer may contain functional groups, such as, for example, hydrazide, amine, alcohol, heterocyclic nitrogen, vinyl, allyl, and carboxylic acid groups, that can be crosslinked using a crosslinking agent. These functional groups may be provided on the polymer or one or more of the copolymers. Alternatively or additionally, the functional groups may be added by a reaction, such as, for example, quaternization. One example is the quaternization of PVP with bromoethylamine groups.

Suitable cross-linking agents include, for example, molecules having two or more epoxide (e.g., poly(ethylene glycol) diglycidyl ether (PEGDGE)), aldehyde, aziridine, alkyl halide, and azide functional groups or combinations thereof. Other examples of cross-linking agents include compounds that activate carboxylic acid or other acid functional groups for condensation with amines or other nitrogen compounds. These cross-linking agents include carbodiimides or compounds with active N-hydroxysuccinimide or imidate functional groups. Yet other examples of cross-linking agents are quinones (e.g., tetrachlorobenzoquinone and tetracyanoquinodimethane) and cyanuric chloride. Other cross-linking agents may also be used. In some embodiments, an additional cross-linking agent is not required. Further discussion and examples of cross-linking and cross-linking agents are found in U.S. Pat. Nos. 5,262,035; 5,262,305; 5,320,725; 5,264,104; 5,264,105; 5,356,786; and 5,593,852, herein incorporated by reference.

In another embodiment, the redox polymer is immobilized by the functionalization of the electrode surface and then the chemical bonding, often covalently, of the redox polymer to the functional groups on the electrode surface. One example of this type of immobilization begins with a poly(4-vinylpyridine). The polymer's pyridine rings are, in part, complexed with a reducible/oxidizable species, such as $[Os(bpy)_2 Cl]^{+/2+}$ where bpy is 2,2'-bipyridine. Part of the pyridine rings are quaternized by reaction with 2-bromoethylamine. The polymer is then crosslinked, for example, using a diepoxide, such as poly(ethylene glycol) diglycidyl ether.

Carbon surfaces can be modified for attachment of an enzyme/redox species or polymer, for example, by electroreduction of a diazonium salt. As an illustration, reduction of a diazonium salt formed upon diazotization of p-aminobenzoic acid modifies a carbon surface with phenylcarboxylic acid functional groups. These functional groups can be activated by a carbodiimide, such as 1-ethyl-3-(3-dimethylaminopropyl)-carbodiimide hydrochloride (EDC).

An optional non-fouling coating can be formed over at least a portion of the electrodes of the fuel cell, typically that portion which would otherwise be exposed to the reaction mixture. The non-fouling coating prevents or retards the penetration of macromolecules, such as proteins, having a molecular weight of 5000 daltons or more, into the electrodes of the SASP device. This can be accomplished using a polymeric film or coating having a pore size that is smaller than the biomolecules that are to be excluded or having anionic and/or cationic functional groups that repel cationic or anionic macromolecules, respectively. Such biomolecules may foul the electrodes and/or the electrolysis layer thereby reducing the effectiveness of the SASP device and altering the expected electrical power generation. The fouling of the electrodes may also decrease the effective life of the SASP device.

For example, the electrodes of the SASP device may be completely or partially coated on their exterior with a non-fouling coating. A preferred non-fouling coating is a polymer, such as a hydrogel, that contains at least 20 wt. % fluid when in equilibrium with the analyte-containing fluid. Examples of suitable polymers are described in U.S. Pat. No. 5,593,852, incorporated herein by reference, and include cross-linked polyethylene oxides, such as polyethylene oxide tetraacrylate and diacrylate. For example, polyethylene oxide ("PEO") chains, typically of 8-18 kilodaltons are terminally modified with reactive groups, such as acrylates and methacrylates. In addition, diesters of PEO can be reacted with star-dendrimer PEO polyamines to form the non-fouling coatings.

Due to the commonly inaccessible nature of the redox centers of redox type enzymes, it is preferred to employ one or more electron mediators. Said electron mediators can be in produced by any known method including, but not limited to, physically admixing the mediator with the enzyme, associating the mediator, either directly or indirectly, to the enzyme to enhance electron transfer from a reactant or desired substrate—enzyme complex to the electrode.

Representative examples of suitable electron mediators for enzyme systems utilizing glucose as a substrate substrates include electron acceptors, such as ferrocene derivatives (see, e.g. U.S. Pat. Nos. 4,545,382 and 4,711,245), ferratin and/or ferratin, cis-platin and similar compounds, colloidal gold compounds and/or derivatives, quinones, various organic dyes, organic redox polymers, (e.g. polyaniline), inorganic redox matrices (e.g., Prussian Blue), etc.

In other preferred embodiments, the preferred mediator compounds are metallocenes, which are organometallic compounds comprising two organic ring structures, each with conjugated unsaturation, and a metal atom sandwiched between the rings, so that the metal atom is in electron-sharing contact with the unsaturated rings. The ferrocene and substituted ferrocene compounds are particularly applicable, as the ferrocenes can mediate electron transfer for a broad range of enzymes.

Ferrocene (dicyclopentadienyl iron), and substituted ferrocene compounds are particularly effective mediators, having pH-independent electrochemically reversible one-electron redox properties, a pH-independent redox potential, slow autoxidation of the reduced form, the absence of any known problems of toxicity or carcinogenicity, a redox potential sufficiently low to avoid excessive interference from competing higher redox potential reactions, satisfactory oxygen insensitivity to avoid excessive interference from oxygen and the ability to be covalently attached to polymer backbones. In a preferred embodiment, no low molecular weight ferrocene specie are present in the polymer since such specie could act as freely diffusing electron transfer mediators.

A further advantage of the ferrocene mediating compounds is the ability to control the redox potential over a wide range through substitution of electron donating or withdrawing groups on the cyclopentadienyl rings. Preferred substituted ferrocenes include, but are not limited to, 1,1'-dimethyl ferrocene, vinyl ferrocene, hydroxyethylferrocene, 1,1'-bis(hydroxymethyl) ferrocene, carboxyferrocene, ferrocenylmonocarboxylic acid, 1,1'-dicarboxyferrocene, and trimethylaminoferrocene.

Other preferred mediator compounds include ruthenocene, dibenzene chromium, phenazine and phenazine derivatives, viologen, riboflavin, p-benzoquinone, and naphthaquinone. In general, redox compounds which can be covalently attached to polymeric backbones and which have redox potentials in the range −0.2 to 0.6 V vs. the SCE are preferred.

In certain preferred embodiments, the donor/acceptor relays are covalently attached to a flexible polymer backbone. In another aspect of the invention the flexible polymer backbone is provided by a siloxane polymer. The unique flexibility of the polysiloxane backbone, which has virtually no energy barrier to rotation, allows these relay moieties to interact intimately with the enzyme molecule and achieve a close contact with the electron transfer moiety(ies).

Generally, the catalysts employed in various embodiments can comprise organometallic cations (electrocatalysts) with standard reduction potentials greater than +0.4 volts. Exemplary electrocatalysts are transition metal complexes, such as osmium, ruthenium, iron, nickel, rhodium, rhenium, and cobalt complexes. Preferred organometallic cations using these complexes comprise large organic aromatic ligands that allow for large electron self exchange rates.

Generally, the electrocatalyst (electron transport mediator or redox polymer) is a substance that facilitates the release of electrons at the electron conductor by reducing the standard reduction potential of the electron mediator.

It is preferred that, when employed, the electrocatalyst is present in a concentration that facilitates the efficient transfer of electrons. Preferably, the electrocatalyst is present at a concentration that makes the enzyme immobilization material conduct electrons. Particularly, the electrocatalyst is present at a concentration of from about 100 mM to about 3 M, more preferably from about 250 mM to about 2.25 M, still more preferably from about 500 mM to about 2 M, and most preferably from about 1.0 M to about 1.5 M.

In other embodiments, a redox polymer modified ion exchange membrane further modified to contain electron transport mediators (e.g., osmium or ruthenium complex, or aromatic organic cations), can be employed. Many electron transport mediators or redox polymers, which are useful in the practice of this invention, are known in the art and described in U.S. Pat. Nos. 5,262,035; 5,262,305; 5,320,725; 5,264,105; 5,356,786; 5,593,852; 5,665,222; 6,294,281; and 6,531,239, which are incorporated herein by reference.

Quinone molecule derivatives are particularly suitable electron mediators. It is preferred that when used for this purpose, the molecule have a quinone skeleton, and in addition, a functional group capable of enabling its association with a polymer or an enzyme ("mediator complex"). A preferred quinone skeleton comprises a naphthoquinone molecule derivative is preferable. Further, a mediator composed of a sodium anthraquinone-2-sulfonate (AQS) derivative or a 2-methyl-1,4-naphthoquinone ($VK_3$) derivative is more preferable. An additional preferred electron mediator is 2,2'-azinobis(3-ethylbenzothiazoline-6-sulfonate) and derivatives thereof.

Preferred polymers for associating the electron mediator group have flexible backbones, for example, polysiloxanes, polyphosphazene, poly(ethylene oxide) and poly(propylene oxide) and/or two or more functional groups selected from the group consisting of an amino group, a carboxyl group, a formyl group, a hydroxyl group, a halogen group, a dihydro-2,5-furandion-1-yl group, and a glycidyl group. Examples of suitable polymers include, inter alia, polyvinyl imidazole, polylysine, polyallylamine, polyvinylpyridine, polypyrrole, polyacrylic acid, polyvinyl alcohol, a graft copolymer of polypropylene and maleic anhydride, and an ortho-cresol novolac epoxy resin. The mediator is preferably modified with a functional group selected from the group consisting of an amino group, a carboxyl group, a chloroformyl group, a succinimide oxycarbonyl group, an alkyl metal sulfosuccinimide oxycarbonyl group, a pentafluorophenyl oxycarbonyl group, a p-nitrophenyl oxycarbonyl group, a hydroxyl group, a formyl group, a halogen group, a maleimide group, an isothiocyanate group, and an oxiranyl group. U.S. Pat. No. 4,224,125 discloses an enzyme electrode, in which the water soluble mediator is in polymeric form in order to remain immobilized near the electrode surface by being too large to diffuse through a retaining membrane into the bulk of the solution. The polymeric redox mediator is reduced by the enzyme catalytic process and reoxidized by the electrode, in the vicinity of which it is contained.

Examples of useful redox polymers and methods for producing them are described in U.S. Pat. Nos. 5,262,035; 5,262,305; 5,320,725; 5,264,104; 5,264,105; 5,356,786; 5,593,852; and 5,665,222, incorporated herein by reference.

It is preferred that the mediator employed is relatively insensitive to the presence of interfering substances, in particular oxygen. It other preferred embodiments, the mediator is attached or otherwise associated with the electrode, in such a fashion as to make it insoluble in the solution to be analyzed, thus preventing the mediating species from diffusing away from the electrode surface.

The mediator molecule (or mediator complex, infra) can be hydrophilic or hydrophobic as required for proper interaction with the enzyme system employed. Two or more kinds of mediator moieties can be used in combination without impairing an effect of the present invention.

Additionally, a spacer molecule can be provided between the functional group and the mediator molecule to maintain an appropriate distance from both. The specific length of the spacer molecule can be suitably changed depending on a kind of the polymer or the enzyme to which the mediator molecule bonds without impairing functions as a mediator. Examples of the spacer molecule include hydrocarbon chain, a polyoxyethylene, a polyethylene glycol, polypropylene glycol, peptides and the like. The spacer molecule preferably has a length within the range of approximately 3 to 50 carbon atoms.

In a preferred embodiment, the cathode is associated with an enzyme(s) or enzyme-assemblies capable of catalyzing the reduction of an oxidizer, preferably oxygen, to water, and optionally a mediator that enhances the electrical contact between the cathode and the enzyme. Examples of such enzymes or enzyme assemblies are laccase and a complex formed of Cytochrome c/Cytochrome oxidase (COx). In the case of laccase, for example, electrons are finally transferred to the oxidizer (e.g., molecular oxygen ($O_2$), to yield water. In this example, the enzyme stores four electrons, and does not release intermediates in the $O_2$ reduction pathway. In the case of Cytochrome c/Cytochrome oxidase (COx), the Cytochrome c-mediated electron transfer to Cytochrome oxidase results also in the four-electron reduction of oxygen to water.

It should be noted that the embodiments describes herein, including those depicted in the accompanying figures, can operate with or without a membrane between the anode and cathode. Operation without a membrane can provide significant advantages with the embodiments of the present invention.

The SASP detection devices/methods can, inter alia, be utilized in a variety of formats bending on the specific application to which it is employed. The following exemplified embodiments are intended to illustrate the invention and shall not be construed as limiting the scope of the invention in any manner.

Example I

Figure 3:
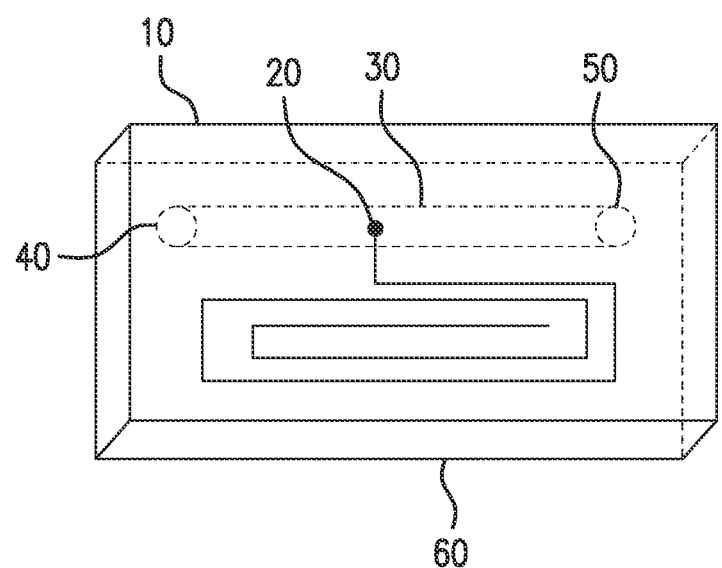
FIG. 3 depicts an embodiment of the present invention wherein a "flow through" type embodiment is employed.
Figure 4:
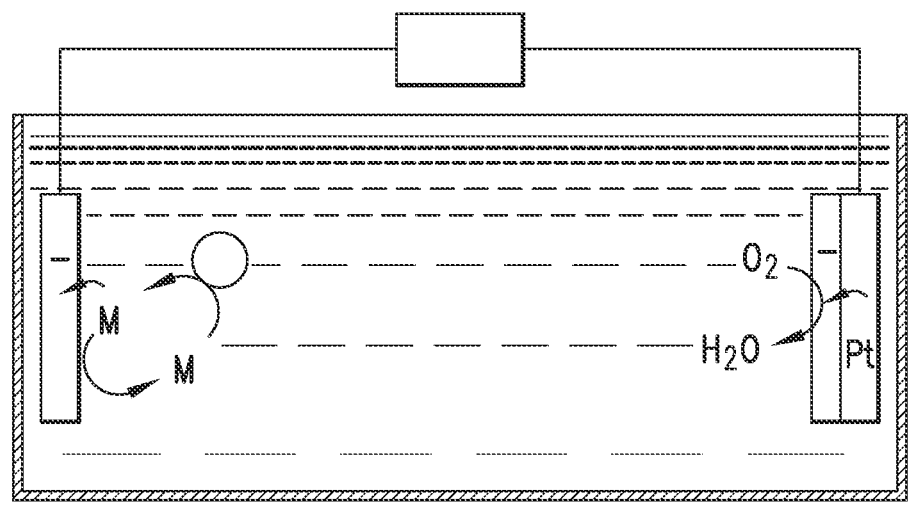
FIG. 4 depicts a biocatalysis redox electrode schematic.
Figure 5:
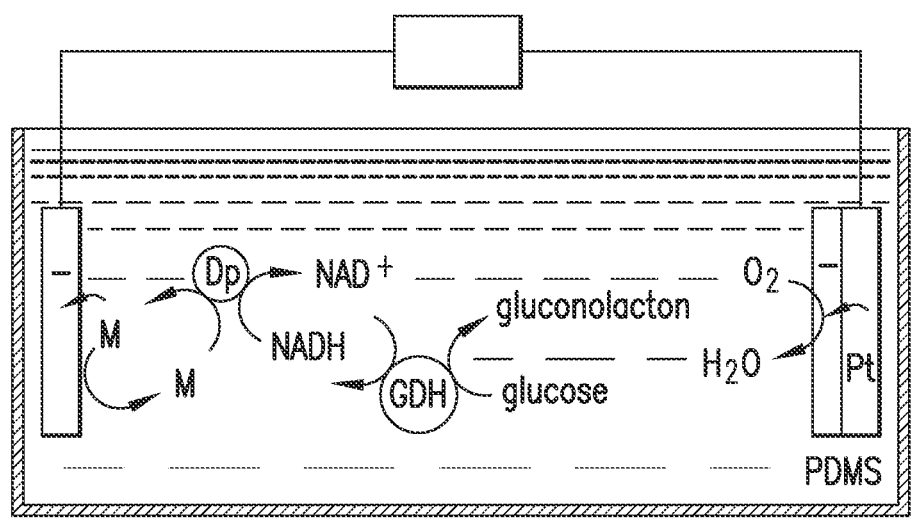
FIG. 5 depicts an alternative biocatalysis redox electrode schematic.

Reference is made to FIG. 3 which schematically depict a SASP device, which can optionally be used in an instrument, and which employs a flow through "chip" design. It must be recognized and understood, however, that many other assemblies/formats can be fabricated, that are based on the concept of the present invention.

FIG. 3 depicts a not-to-scale representative example of a type of "flow through" type embodiment in accordance with the present invention. Liquids are able to flow from access port 40 (which is in communication with flow path 30 to access port 50 (which is also in communication with flow path 30).

Figure 6:
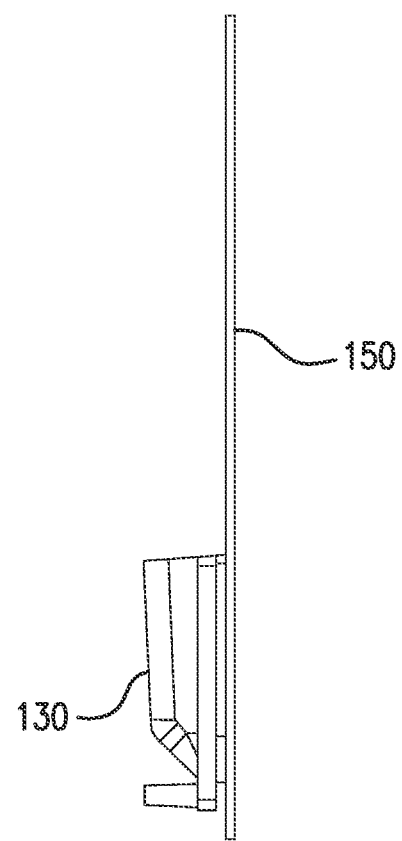
FIG. 6 depicts an electrode-provided disposable reaction chamber for a preferred embodiment of the invention in side elevation.
Figure 7:
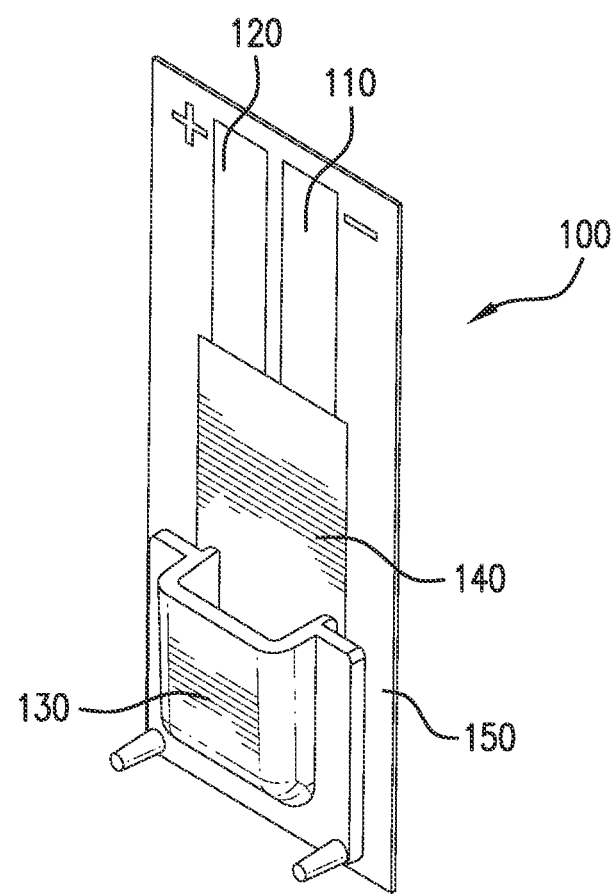
FIG. 7 depicts the reaction chamber of FIG. 11 in front elevation.

Located within flow path 30, is one or more reaction zones (20) (an example of which is representatively depicted in FIG. 6). Reaction zone(s) 20 comprise one of more electrodes, a representative non-limiting example of which are depicted in FIG. 7.

In operation, sample suspected of containing target analyte (not shown) is contacted with reagent (not shown) containing a first antibody which is conjugated to an essential element of the enymatic/redox reaction of the present invention (e.g., glucose oxidase "GOx"). Optionally, other reagents can be admixed as required. GOx conjugated antibody, which antibody is bound to target analyte is present (not shown), is introduced to chip 10 via access port 40. Sample volume traverses flow path 30, exiting via access port 50. During such traversing, sample volume traverses reaction zone 20. The number of reaction zones (20) is dependent upon the test(s) to be performed and the application to which such test(s) is applied and can vary as necessary. The number of reaction zones can be within a range of 1-1000, preferably between 1-100, more preferably between 1-50, more preferably between 1-25, more preferably between 2-20 and most preferably between 1-10 or 2-10 or alternatively, 1-5 or 2-5.

On reaching reaction zone(s) 20, any target analyte molecule present in the sample should be captured by a second antibody, so "immobilizing" the labeled "sandwich" so produced. This sandwich immobilization in zone 20, thereby positions the enzyme in close proximity to the electrode(s) within zone 20, thereby enabling the redox biocatalysis and generation of electron flow, which in turn powers, directly or indirectly, a signaling event in the presence of enzyme substrate (not shown). Enzyme substrate (not shown) is added, preferably via access port 40.

In contrast to, for example, the glucose biosensors and other diagnostic devices of the prior art, the sandwich capture of the enzyme/redox element in reaction zone 20 is expressly not for the purpose of detecting the substrate of the captured enzyme. Rather, the localization of, in this example, the antibody-conjugated GOx, does not detect the presence or amount of glucose, but instead, is used as an in situ generated biofuel cell, which when glucose is added (e.g, via access port 40), the enzyme redox system is capable of producing electron flow and thereby, directly or indirectly, present a system capable of generating a signal in accordance with the various embodiments of the present invention. Thus, absent the addition of the enzyme substrate, the signaling event cannot occur (or alternatively, occurs at a sufficiently low level, relative to when the substrate is present, so as to allow a distinguishable signal).

In a preferred operation, the sample containing (or suspected of containing) the target analyte, is suspended in an appropriate buffer for the particular system employed, and introduced (manually or automated means) into the flow through chip. The substrate is captured by a capture moiety(ies) associated with said RF circuitry. Suitable capture moieties include any moiety capable of the selective capture of the target/enzyme system in a manner to localize the reaction in the proximity of the RF circuit/electrode complex. Preferred capture moieties include antibodies, and more preferably monoclonal antibodies. The capture complex is preferably designed to associate the target analyte with the enzyme complex (or component thereof) with the electrode/circuit complex In a preferred embodiment the flow through chip is optionally flushed to remove unbound reagents. The specific substrate for the enzyme/redox complex is then added to the flow through chip port (50), so as to allow for the catalytic generation of electrons through the catalyst/redox reaction. Thus, where the target analyte is present, the resulting complex will include all necessary catalyst/redox system components in association with the electrode/RF circuit complex and, thereby result in the generation of a detectable RF signal.

In a preferred embodiment, the enzyme/redox substrate is provided in molar excess. In a more preferred embodiment, the substrate is provided in a 10 fold molar excess. In a more preferred embodiment, the substrate is provided in a 100 fold molar excess. In a more preferred embodiment, the substrate is provided in a 1,000 fold molar excess. In a more preferred embodiment, the substrate is provided in a 10,000 fold molar excess. In a more preferred embodiment, the substrate is provided in a 100,000 fold molar excess. In a more preferred embodiment, the substrate is provided in a 1,000,000 fold molar excess. In a more preferred embodiment, the substrate is provided in an amount in excess of a 1,000,000 fold molar excess.

Example II

In contrast to, for example, the glucose biosensors and other diagnostic devices of the prior art, the sandwich capture of the enzyme/redox element in a reaction zone is expressly not for the purpose of detecting the substrate of the captured enzyme. Rather, the localization of, in this example, the antibody-conjugated GOx, does not detect the presence or amount of glucose, but instead, is used as an in situ generated biofuel cell, which when glucose is added the enzyme redox system is capable of producing electron flow and thereby, directly or on directly, present a system capable of generating a signal in accordance with the various embodiments of the present invention. Thus, absent the addition of the enzyme substrate, the signaling event cannot occur (or alternatively, occurs at a sufficiently low level, relative to when the substrate is present, so as to allow a distinguishable signal).

In a preferred embodiment, the reaction zone comprises electrodes associated with RF circuitry in a manner suitable to allow the transfer of electrons from said the reduction/oxidation of the substrate by the redox enzyme system, such that the flow of electrons functions to provide the poser required by the RF circuitry to produce a detectable signal.

In a preferred embodiment, the enzyme/redox substrate is provided in molar excess. In a more preferred embodiment, the substrate is provided in a 10 fold molar excess. In a more preferred embodiment, the substrate is provided in a 100 fold molar excess. In a more preferred embodiment, the substrate is provided in a 1,000 fold molar excess. In a more preferred embodiment, the substrate is provided in a 10,000 fold molar excess. In a more preferred embodiment, the substrate is provided in a 100,000 fold molar excess. In a more preferred embodiment, the substrate is provided in a 1,000,000 fold molar excess. In a more preferred embodiment, the substrate is provided in an amount in excess of a 1,000,000 fold molar excess.

In a preferred embodiment, the RF signal is detected by a hand held detector. In a more preferred embodiment, the RF signal is detected by a battery powered hand held detector. In a more preferred embodiment, the RF signal is detected by a wristwatch-styled detector.

Example III

In a preferred operation, the sample containing (or suspected of containing) the target analyte, is suspended in an appropriate buffer for the particular system employed, and introduced (manually or automated means) into the flow through the device body. The substrate is captured within reaction zone by a capture moiety(ies) associated, directly or indirectly, with electrodes which in turn are associated, directly or indirectly, with an electronic circuit (e.g., RF circuitry). Suitable capture moieties include any moiety capable of the selective capture of the target/enzyme system in a manner to localize the reaction in the proximity of the RF circuit/electrode complex. Preferred capture moieties include nucleic acids and/or antibodies, and more preferably monoclonal antibodies. The capture complex is preferably designed to associate the target analyte with the enzyme complex (or component thereof) with the electrode/circuit complex.

In a preferred embodiment the flow through chip is optionally flushed to remove unbound reagents. The specific substrate for the enzyme/redox complex is then added passed thru the device, so as to allow for the catalytic generation of electrons through the catalyst/redox reaction. Thus, where the target analyte is present, the resulting complex will include all necessary catalyst/redox system components in association with the electrode/RF circuit complex and, thereby result in the generation of a detectable RF signal.

In a preferred embodiment, the enzyme/redox substrate is provided in molar excess. In a more preferred embodiment, the substrate is provided in a 10 fold molar excess. In a more preferred embodiment, the substrate is provided in a 100 fold molar excess. In a more preferred embodiment, the substrate is provided in a 1,000 fold molar excess. In a more preferred embodiment, the substrate is provided in a 10,000 fold molar excess. In a more preferred embodiment, the substrate is provided in a 100,000 fold molar excess. In a more preferred embodiment, the substrate is provided in a 1,000,000 fold molar excess. In a more preferred embodiment, the substrate is provided in an amount in excess of a 1,000,000 fold molar excess.

Example IV

In this particular embodiment, an oxidation reaction of glucose proceeds at an anode, and a reduction reaction of oxygen proceeds at a cathode. An enzyme required for glucose oxidation (glucose oxidase (GOx), in this case) and a mediator act at the anode to take electrons discharged from the oxidation reaction of glucose out of a system. The GOx is associated with the anode through the SASP reaction at the reactive zone (see, e.g., FIG. 1 at element 20). The electrons are taken out of the system through the depicted circuit, which circuit can produce a variety of signals in accordance with the present invention, including, inter alia, a RF signal. Glucose is used as a "fuel" in this example.

Example V

In this particular embodiment, an oxidation reaction of glucose proceeds at an anode, and a reduction reaction of oxygen proceeds at a cathode. An enzyme required for glucose oxidation (glucose dehydrogenase (GDH), in this case), a coenzyme (NADH), diphorase, and a mediator, act at the anode to take electrons discharged from the oxidation reaction of glucose out of a system. The GDH is associated with the anode through the SASP reaction at the reactive zone (see, e.g., FIG. 1 at element 20). The electrons are taken out of the system through the depicted circuit, which circuit can produce a variety of signals in accordance with the present invention, including, inter alia, a RF signal. Glucose is used as a "fuel" in this example.

Figure 8:
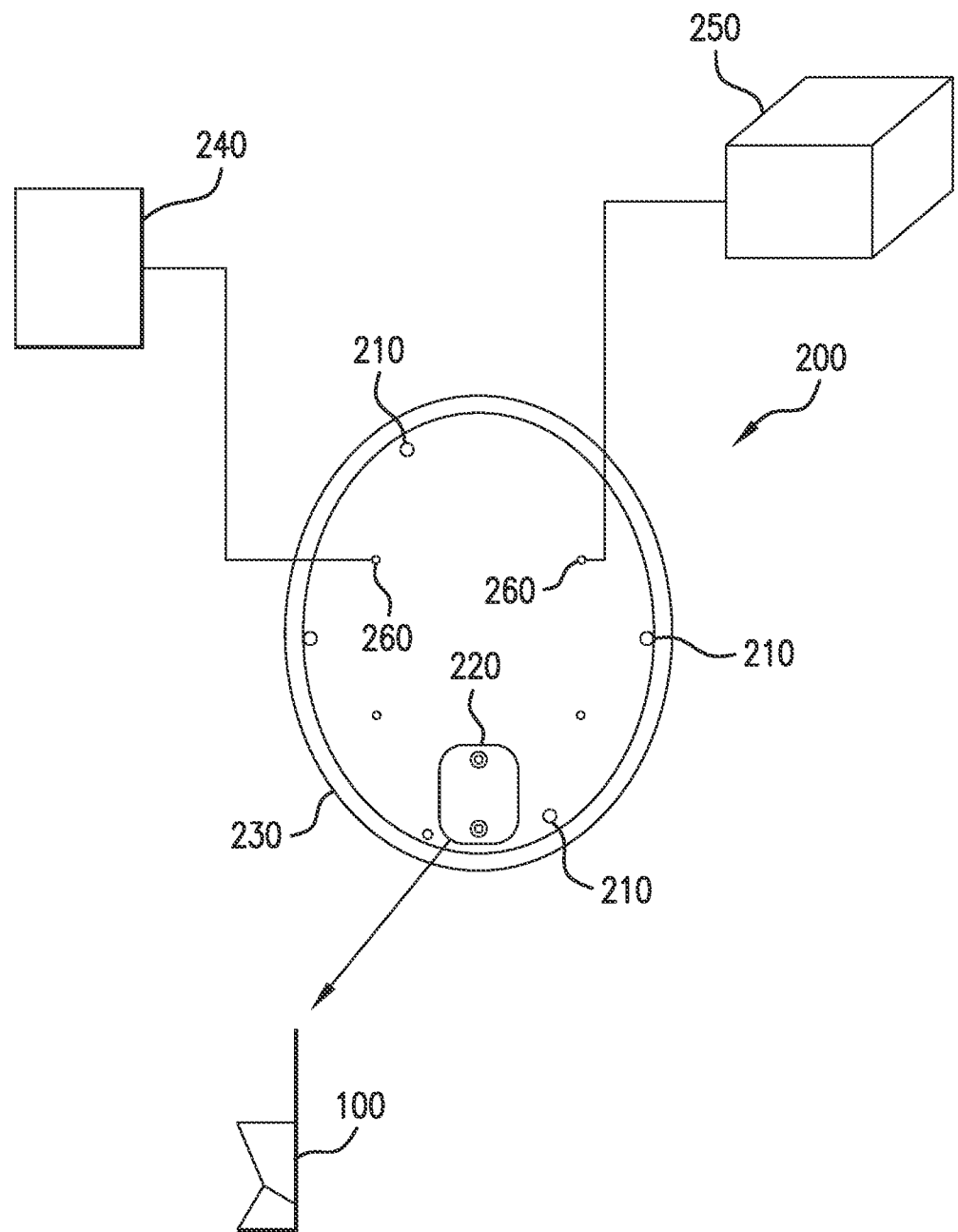
FIG. 8 depicts a field deployable device for receiving a reaction chamber cartridge and detecting electric potential developed between the electrodes thereof in bottom elevation.
Figure 9:
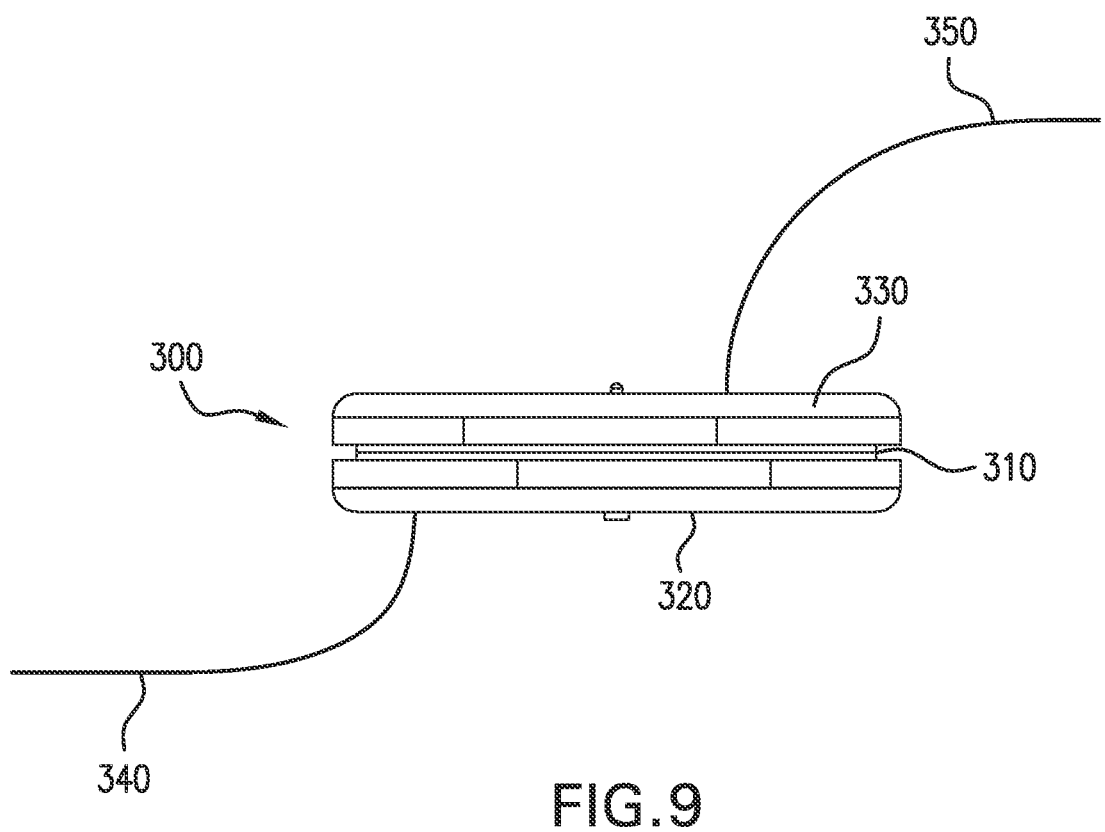
FIG. 9 depicts a field deployable device for measuring potential developed across electrodes of a disposable reaction chamber from side elevation.

At a preferred anode of the SASP devices and methods of the present invention, including, for example, the systems of FIGS. 8 and 9, one or more sugars, alcohols, and/or carboxylic acids, typically found in the biological system, are electrooxidized. Preferred anode enzymes for the electrooxidation of the anode reductant include, for example, glucose dehydrogenase, glucose oxidase, galactose oxidase, fructose dehydrogenase, quinohemoprotein alcohol dehydrogenase, pyranose oxidase, oligosaccharide dehydrogenase, and lactate oxidase.

One embodiment of the anode is formed using a high surface area graphite fiber/carbon black electrode using polypropylene or polytetrafluoroethylene as a binder. The anode redox polymer and anode enzyme are then disposed on the anode.

The anode potential can be limited by the (a) redox potential of the anode enzyme, (b) the concentration of the anode reductant at the anode, and (c) the redox potential of the anode redox polymer. Reported redox potentials for known anode enzymes range from about −0.4 V to about −0.5 V versus the standard calomel electrode (SCE). Typically, the preferred anode redox polymers have a redox potential that is at least about 0.1 V positive of the redox potential of the anode enzyme. Thus, the preferred anode redox polymer can have a redox potential of, for example, about −0.3 V to −0.4 V (SCE), however, the potential of the anode redox polymer may be higher or lower depending, at least in part, on the redox potential of the anode redox enzyme.

In some embodiments, one or more additional enzymes are provided in proximity to or disposed on the anode. The additional enzyme or enzymes break down starch, cellulose, poly- and oligosaccharides, disaccharides, and trisaccharides into the sugars, alcohols, and/or carboxylic acids that are used as a substrate. Examples of such catalysts include α-amylase from *Bacillus stearothermophilus*, β-amylase from *Aspergillus*, glucan-1,4-α-glucosidase from *Rhizopus niveus*, cellulase from *Aspergillus niger*, endo-1-3(4)-β-glucanase from *Aspergillus niger*, dextranase from *Leuconostoc mesenteroides*, α-glucosidase from *Bacillus stearothermophilus*, β-glucosidase from *Caldocellum saccharolyticum*, β-galactosidase from *aspergillus*, β-fructofuranosilidase from yeast, and lactase from *Aspergillus oryzae*.

Example VI

Reference may be had to FIGS. 6 and 7, which show, from side elevation and front elevation, together, an exemplary disposable reaction chamber cartridge of this invention. Bearing in mind that a specific feature of this invention is the ability to employ it, as a self powered device, in the field, the use of disposable cartridges or similar low cost, hardy reaction chambers becomes important. As shown in FIG. 6, the reaction chamber is mounted on a flange 150, to which is attached a reaction chamber containment area 130. The containment area, which, together with the front surface of flange 150, defines the reaction chamber, is conventionally made of molded or extruded plastic at low cost.

As more fully shown in FIG. 7, the reaction chamber defined by enclosure 130 and mounting flange 150 is of a small volume. An important aspect of this invention is the ability to test small volumes of sample and target, and generate a detectable signal. Cathode 110 and anode 120 are painted onto the surface of flange 150, or otherwise mounted thereon, and extend into the reaction chamber. They may be protected by membrane 140. In a preferred embodiment, cathode 110 is covered by a membrane that may be sprayed or painted on, such as one prepared from a proton exchange membrane, like Nafion™.

Example VII

In many embodiments of this invention, the disposable reaction chamber of FIGS. 6 and 7 is desirably read in the field, where the sample is obtained, and where the signal reflecting the presence and amount of target is taken. For these purposes, a self-powered device, containing the necessary hardware and provided with appropriate software may be deployed, designed to receive the disposable reaction chamber of FIGS. 6 and 7, such as that shown from the underside in FIG. 8. This device 200 is made of rugged plastic, and connected through a cap of similar material (330 of FIG. 9) which together harbor and protect the necessary hardware, software and firmware, including the meter or sensing device to detect potential or current flow between cathode 110 and anode 120. To this end, the bottom half of the detection device 200 is secured through holding devices (screws, bolts, rivets, etc.) to top 330 illustrated in FIG. 9. As shown, the device 200 is equipped with ports 260 from which leads may be connected to various auxiliary devices, such as RFID device 240, or computer (laptop or iTouch™ or similar PDA or mobile phone) 250. The signal, which may be read directly from a meter provided in device 200, may be stored in or broadcast to distant locations via the auxiliary devices.

The device 200 is provided with a receptacle or opening 220 intended to receive disposable reaction chamber 100. As shown, the receptacle or slot is provided with hard wired electrical contacts so as to receive current flow from cathode 110 and anode 120. These may be run to a meter or gap potential measurement device, or as noted, a more sophisticated device, such as a computer, or a data storage means which may subsequently be accessed for the signals detected, or may transmit the signal and associated data, may be connected through simple electronic connections, such as a USB cable.

The complete field deployable device for receiving, measuring and sending the signal upon addition of the substrate to the reaction chamber is illustrated in FIG. 9, where the device is indicated at 300. The base, with cartridge inserted, at 320, is secured, as indicated, to a damage resistant top 330. These sandwich and protect the interior of the device, including the wiring, software and hardware necessary to detect the potential as a signal, generally indicated at 310. Leads may extend from the device, 340 and 350, for interconnection with auxiliary devices.

Example VIII

In one embodiment, the cathode reduces gaseous $O_2$ that is typically dissolved in the biological fluid or originating from the air. In another embodiment of the fuel cell, hydrogen peroxide is formed in a non-enzyme-catalyzed electrode reaction or in an enzyme-catalyzed reaction on or off the cathode and then the hydrogen peroxide is electroreduced at the cathode. Preferred cathode enzymes for the reduction of $O_2$ and $H_2O_2$ include, for example, tyrosinase, horseradish peroxidase, soybean peroxidase, other peroxidases, laccases, and/or cytochrome C peroxidases.

One embodiment of the cathode includes a porous membrane formed over at least a portion of cathode. The porous membrane has an $O_2$ and/or $H_2O_2$ permeable, hydrophobic outer surface and an $O_2$ and/or $H_2O_2$ permeable hydrophilic inner surface. In another embodiment, the cathode includes an outer layer of a hydrophobically modified porous silicate carbon composite, formed of an alkyltrialkoxysilane precursor, and carbon black. The inner layer is a hydrophilic silica-carbon composite. In another embodiment, the electrode is a microporous Teflon PTFE bound acetylene/carbon black electrode. The inner surface is plasma processed to make it hydrophilic. The redox polymer and enzyme are deposited on the inner surface of the cathode. When the cathode is exposed to $O_2$ originating in blood or a body fluid, the cathode may only include hydrophilic surfaces in contact with the $O_2$ transporting biological fluid.

The cathode potential can be limited by the (a) redox potential of the cathode enzyme, (b) the concentration of the cathode oxidant at the cathode, and (c) the redox potential of the cathode redox polymer. Reported redox potentials for known $O_2$ reducing enzymes range from about +0.3 V to about +0.6 V versus the standard calomel electrode (SCE).

Typically, the preferred cathode redox polymer has a redox potential that is at least about 0.1 V negative of the redox potential of the enzyme. Thus, the preferred redox polymer has redox potential of, for example, about +0.4 to +0.5 V (SCE), however, the potential of the cathode redox polymer may be higher or lower depending, at least in part, on the redox potential of the cathode redox enzyme.

For osmium complexes used as the cathode redox polymer, typically, at least four, usually, at least five, and, often, all six of the possible coordination sites of the central osmium atom are occupied by nitrogen atoms. Alternatively, for complexes of ruthenium used as the cathode redox polymer, typically, four or fewer, and, usually, three or fewer of the possible coordination sites are nitrogen occupied.

There are several advantages to an enzyme electrode system based on a crosslinked redox polymer. First, the use of crosslinked films on the electrode surface eliminates the requirement for a membrane which is often required in conventional systems to confine the enzyme to a small volume close to the electrode surface. Thus, the use of crosslinked redox films tends to simplify the design and the manufacture of the enzyme electrode. Second, the process by which the electrodes are produced is relatively simple, reproducible and can be easily automated. Third, the enzyme may be stabilized by its interaction with the polymer matrix, thus retarding thermal denaturation. Also, it may be physically protected from attack by proteases in solution which are too large to diffuse through the polymer film. Fourth, the versatility of these materials allows the tailoring of properties for specific applications. For example, the redox potential, the hydrophilicity and the charge on the polymer may be adjusted as may the crosslinking method. Fifth, the transport of interfering electroreactive substances to the electrode surfaces and/or their adsorption on these surfaces can be retarded by appropriate design of the polymer. Sixth, the resulting electrodes are in general mechanically rugged and typically exhibit excellent stability during storage. Seventh, although enzymes are known to rapidly denature on many surfaces, the polymer apparently tends to protect the enzymes from the surface of the electrode. Thus, virtually any electrode surface may be used for these enzyme electrodes. Additionally, such polymers in general appear to be substantially biocompatible.

In one preferred embodiment, the water soluble crosslinking agent polyethylene glycol diglycidylether (PEG-DGE, FIG. 3) is used to react with redox compounds with amine functions and with amine functions of the lysine groups of the enzyme. The reaction between epoxides and amines is particularly advantageous since the reaction (1) releases no low molecular weight species; (2) does not greatly change the local pH; (3) does not greatly change the charge on either the redox compound or the enzyme; and (4) is compatible with a number of different enzymes. PEG-DGE is also commercially available in a number of chain lengths. The reaction between PEG-DGE and amines proceeds very slowly in dilute aqueous solution. Thus, all the reactants may be combined in a single solution before the application step which greatly simplifies the manufacture of the electrodes. The crosslinking reaction may then proceed to completion when the solution is dried on the surface of the electrode. The cure time for the film is 24 to 48 hours at room temperature.

Example IX

An exemplary protocol for the immobilization of an enzyme, in this example, glucose oxidase, is as follows:

A. Carbodiimide Treatment:

1. Cut out pieces of electrode of suitable size from the sheet of Prototech electrode material.

2. Immerse the electrodes in ethanol for about 5 minutes to ensure thorough wetting of the PTFE coated binder and backing.

3. Remove the electrodes from the ethanol and wash them thoroughly with distilled water to remove all traces of ethanol.

4. Prepare 5 ml (or less) of a 0.15M solution of 1-cyclohexyl-3-(2-morpholino)carbodiimide p-methyltoluene sulphonate in 0.1M pH 4.5 acetate buffer and place the electrodes in this for 90 minutes at room temperature. Gentle agitation with a mechanical shaker may be used. Should the electrodes float on the surface of the solution then they have not been sufficiently wetted, and the treatment should be repeated from step 2.

5. Remove the electrodes and wash them thoroughly with distilled water. Place them in a freshly prepared solution of glucose oxidase (5.0 mg/ml) in pH 5.6 acetate buffer for 90 minutes at room temperature with gentle mechanical shaking.

6. Remove the electrodes from the enzyme solution and rinse them thoroughly with 0.1M acetate buffer. The electrodes are now ready for use.

7. Store the electrodes at 4.degree. C. in 0.1M pH 5.6 acetate buffer.

B. Carbonyldiimidazole Treatment:

1. Carry out step 1 above and omit steps 2 and 3.

2. Prepare a solution of N,N'-carbonyldiimidazole in anhydrous dimethyl formamide (40 mg/ml).

3. Place the electrodes in this solution for 90 minutes at room temperature with gentle mechanical shaking if desired.

4. Remove the electrodes from the solution and dry off the excess carbonyldiimidazole solution before placing them in a freshly prepared solution of glucose oxidase for a further 90 minutes.

5. Carry out steps 6 and 7 above.

C. DFDNB Treatment:

1. Carry out steps 1-3 under A above.

2. Wash the electrodes thoroughly in sodium borate buffer (0.1M, pH 8.5).

3. Prepare a solution of 1,6-dinitro-3,4-difluorobenzene in methanol (0.1021 g/5 ml) and place the electrodes in this for 10 minutes at room temperature.

4. Remove the electrodes and wash them thoroughly with borate buffer before placing them in a solution of glucose oxidase for a further 90 minutes at room temperature.

5. Carry out steps 6 and 7 under A above.

Other types of coupling agent may be used for the immobilisation process, including bifunctional agents of variable chain length, for example diimidates such as dimethylmalonimidate or dimethylsuberimidate.

In the alternative, it has been found that simple adsorption of the enzyme onto the resin-bonded platinised or palladised carbon powder support, i.e. without cross-linking, is effective with some enzymes, and in particular with glucose oxidase.

Usually, but not necessarily, the surface layer of immobilised enzyme will be physically protected by the application of a suitably porous, e.g. polycarbonate, film or membrane which must, of course, be permeable by the enzyme substrate (glucose) which is to be determined. Such membranes are somewhat disadvantageous in increasing the response time of the sensor, but nevertheless even with such a membrane the present sensors are capable of response times comparable with, and in many cases, substantially better than, conventional enzyme electrodes.

The physical dimensions of representative electrodes utilized in conjunction with other preferred embodiments, as well as the operational parameters, such as the output power and voltage, are, at least in part, a function of the components of SASP devices. The open circuit voltage of the SASP devices can range from, for example, 0.5 volts to 1.2 volts, however, the SASP devices of the invention can also produce larger or smaller voltages. The voltage at the maximum power point can range from, for example, 0.4 to 0.8 volts. In addition, two or more fuel cells may be combined in series and/or in parallel to form a composite SASP devices with a larger voltage and/or current. The volumetric output power density of the SASP devices can range from, for example, about 0.5 mW/cm$^3$ to about 5 mW/cm$^3$, however, SASP devices can also be formed with higher or lower volumetric output power density. The gravimetric output power density can range from, for example, about 5 mW/g to about 50 W/g, however, fuel cells can also be formed with higher or lower gravimetric output power density. The output power density depends on the flow of fluid through the SASP devices. Generally, increasing the rate of flow increases the output power density.

Example X

The following non-limiting example of carbonization is provided. As the carbon powder there may be used any suitable carbon or graphite powder which readily permits the subsequent immobilisation of the enzyme, and to this end, carbon powders should be used having a high density of functional groups, such as carboxylate, amino and sulphur-containing groups, on the surface, as opposed to the more vitreous and glassy carbons, which bind enzymes only poorly. Particle size may range from 3 to 50 nm, more usually 5 to 30 nm.

Platinum (or palladium) may be deposited on the carbon particles in any convenient fashion, e.g. vapour phase deposition, electrochemical deposition or simple adsorption from colloidal suspension (which is preferred for certain embodiments) to give platinum group metal loadings of from 1 to 20% by weight, based on the weight of carbon, preferably from 5 to 15%. These limits are, however, practical rather than critical. Below about 1% platinum group metal the output signal falls to a level which, in practical terms, is too low to be measured except by very sensitive apparatus. Above about 20%, the loading of platinum group metal becomes uneconomic, with little additional benefit in terms of response time, sensitivity etc. Indeed with extremely high metal loadings the sensitivity begins to fall. In the preferred technique the carbon powder is platinised or palladised by the oxidative decomposition of a platinum or palladium compound such as chloroplatinic acid, or more preferably still a complex of platinum or palladium with an oxidisable ligand, in the presence of the carbon powder, thereby to deposit colloidal size platinum or palladium direct onto the surface of the carbon particles, in the manner taught, for example, in GB-A-1,357,494, U.S. Pat. Nos. 4,044,193 and 4,166,143.

Following platinisation or palladisation the platinised or palladised carbon powder is moulded using a suitable water-repellent bonding resin, preferably a fluorocarbon resin such as polytetrafluoroethylene to form either a completely self-supporting porous moulded structure consisting essentially of said resin bonded platinised or palladised carbon powder particles, or more usually a porous moulded surface layer of such resin-bonded particles bonded to an electrically conductive substrate, e.g. of metal, carbon or graphite. A particularly preferred substrate material for the moulded, resin-bonded platinised carbon layer is carbon paper as taught by U.S. Pat. No. 4,229,490, or an open pore carbon cloth as taught by U.S. Pat. No. 4,293,396. In order to retain maximum porosity the amount of resin used as the binding agent should be the minimum required to provide mechanical integrity and stability to the electrode layer, such layer usually having a thickness no more than about 0.1 to 0.5 mm, although greater thicknesses may be employed. Subject to the requirements of structural integrity, mechanical strength, and porosity, amounts of binding resin are not critical and may range from as little as 5 or 10% by weight, based on the amount of platinised or palladised carbon powder, up to as much as 80%, but with the amount more usually in the range 30 to 70% by weight. A variety of resins may be used, including resins which are conducting or semi-conducting, but preferred are synthetic fluorocarbon resins, particularly polytetrafluoroethylene. In view of the small but essential requirement for oxygen in the oxidation process it is essential that the binder be permeable to oxygen.

In an alternative, disclosed in U.S. Pat. No. 4,293,396, the platinised carbon particles are impregnated into a preformed porous carbon cloth and bonded therein using the fluorocarbon resin, preferably polytetrafluoroethylene. It is to be understood, however, that the present invention is not limited to the use of Prototech materials, but embraces other similar substrate materials comprising resin-bonded and moulded platinised or palladised carbon powder. In particular, it is contemplated that there also may be used materials of the type disclosed as fuel cell electrodes in U.S. Pat. No. 4,229,490, that is to say carbon paper electrodes of the type comprising a carbon paper support member, preferably impregnated with a water-repellent resin such as polytetrafluoroethylene, and onto which is deposited, e.g. by screen printing, a resin bonded catalyst layer comprising a uniform mixture of platinum black and carbon or graphite particles bonded with a water-repellent resin, preferably again polytetrafluoroethylene.

The immobilisation of the enzyme on the surface of the resin-bonded, platinised or palladised carbon substrate can be carried out using a variety of well established immobilisation techniques, for example, covalent bonding with a carbodiimide or a carbonyldiimidazole reagent, covalent bonding with 1,6-dinitro-3,4-difluorobenzene (DFDNB), or cross-linking with glutaraldehyde.

Example XI

Capture 2 oligonucleotide #100003_15_amino (5' amino modified 15 nucleotides long) is synthesized using standard phosphoramidite chemistry (TriLink BioTechnologies, Inc. San Diego, Calif.).

5'-AGGATGACACCTAGA-3'

The oligonucleotide is then purified using NAP-5 column (0.1M/0.15M buffer of NaHCO$_3$/NaCl, pH 8.3). 0.2 ml of 100 uM water solution of oligonucleotide #100003_15_amino is loaded on a column. After 0.3 ml push 0.8 ml of eluant is collected and quantified. Based on A$_{260}$ reading more than 90% of recovery is observed. Purified oligonucleotide subsequently is chemically modified using Succinimidyl 4-formylbenzoate (C6-SFB). 790 ul of purified oligonucleotide and 36 ul of C6-SFB (20 mM in DMF) are mixed (1:40 ratio) and incubated at room temperature for 2 hrs.

Reaction product is cleaned up using 5 ml HiTrap (GE) desalting column and 1.5 ml eluant is collected. Based on A$_{260}$ reading more than 80% recovery of oligonucleotide-C6-SFB is observed.

A Glucose Oxidase from *Aspergillus niger* (Fluka, 49180) is purified using NAP-5 column (1×PBS buffer, pH 7.2).

0.25 ml of Glucose Oxidase (5 mg/ml) is loaded on a column. After 0.25 ml push 1 ml of eluant is collected and quantified. Based on A$_{280}$ reading 1.25 mg/ml (7.8 uM) Glucose Oxidase recovery is observed.

Purified Glucose Oxidase subsequently is chemically modified using Succinimidyl 4-hydrazinonicotinate acetone hydrazone (C6-SANH). 950 ul of 7.8 uM of Glucose Oxidase and 10.4 ul of C6-SANH (10 mM in DMF) are mixed (1:20 ratio) and incubated at room temperature for 30 min. Reaction product is cleaned up using 5 ml HiTrap (GE) desalting column and 1.25 ml eluant is collected. BCA/BSA (BCA assay from Pierce, cat #23225/23227; Bradford assay from Pierce, cat #23236) assay is used to determine the concentration of recovered Glucose Oxidase-C6-SANH (typically ~1 mg/ml, yield more than 95%).

The conjugation of Glucose Oxidase and oligonucleotide is typically achieved by mixing the 1010 ul of Glucose Oxidase-C6-SANH and 750 ul of oligonucleotide-C6-SFB in a molar ratio 1:2 and incubated overnight at room temperature. The resulting conjugates are analyzed on TBE/UREA gel, and purified using MiniQ FPLC. Standard gradient approach is utilized using MiniQ 4.6/50 PE column (GE Healthcare, cat #17-5177-01), 0.25 ml/min flow rate, detection at 280 nm. buffer A: 20 mM Tris/HCl, pH 8.1, buffer B: 20 mM Tris/HCl, NaCl 1M, pH 8.1. BCA/BSA assay is used to determine the concentration of recovered Glucose Oxidase-capture 2 oligonucleotide conjugate (~3 ml of eluant, 0.15 mg/ml).

Example XII

Preparation of DNA-Enzyme Conjugates

Capture 2 oligonucleotide #100003_15_amino (5' amino modified 15 nucleotides long) is synthesized using standard phosphoramidite chemistry (TriLink BioTechnologies, Inc. San Diego, Calif.).

5'-AGGATGACACCTAGA-3'.

The oligonucleotide is then purified using NAP-5 column (0.1M/0.15M buffer of NaHCO$_3$/NaCl, pH 8.3). 0.2 ml of 100 uM water solution of oligonucleotide #100003_15_amino is loaded on a column. After 0.3 ml push 0.8 ml of eluant is collected and quantified. Based on A$_{260}$ reading more than 90% of recovery is observed. Purified oligonucleotide subsequently is conjugated with Glucose Oxidase using a commercially available Lightning-Link Glucose Oxidase Conjugation Kit (Innova Biosciences Ltd, Cambridge, UK. Cat #706-0010) following the manufacturers protocol with some modifications. Briefly, 4 ul of modifier is added to 40 ul of amino modified oligo (50 uM in water). Resulted 44 ul of solution is added into ½ vial of LL-Gox and incubated overnight at room temperature in dark. After incubation 5 ul of quencher is added to the reaction mixture and incubated for 30 min at room temperature in dark.

The resulting conjugate subsequently is purified via Micron YM-100 spin column (Millipore, USA) to remove an access of amino modified oligonucleotide. Briefly, 50 ul of conjugate is loaded into the column and centrifuge at 8000 rpm for 8 min. Flow through is discarded. 200 ul of 1× (50 mM) PBS (50 mM, pH 7.5) is added to a column and centrifuge at 8000 rpm for 8 min. Flow through is discarded. 50 ul of 1×PBS (50 mM, pH 7.5) is added to a column, carefully mixed using a vortex for a few seconds and centrifuge at 2000 rpm for 2 min. 50 ul of purified capture 1 oligonucleotide. Enzyme conjugate is collected and saved at 4° C. for future use.

Example XIII

Preparation of DNA Immobilized-Oligo (Dt)$_{25}$ Magnetic Beads

Capture 1 oligonucleotide #100003_19_polyA (36 nucleotides long) is synthesized using standard phosphoramidite chemistry (TriLink BioTechnologies, Inc. San Diego, Calif.).

5'-GTGATCGGGAGTGTGTCCAAAAAAAAAAAAAAAAA-3'

The oligonucleotide is then purified using NAP-5 column (0.1M/0.15M buffer of NaHCO$_3$/NaCl, pH 8.3). 0.2 ml of 100 uM water solution of oligonucleotide #100003_15_amino is loaded on a column. After 0.3 ml push 0.8 ml of eluant is collected and quantified. Based on $A_{260}$ reading more than 90% of recovery is observed. Purified oligonucleotide subsequently is annealed with Oligo $(dT)_{25}$ magnetic beads (Dynabeads Oligo $(dT)_{25}$, Invitrogen Corporation, Carlsbad, Calif. Cat #610). Briefly, 30 ul of magnetic beads suspension is washed twice with 1× Binding buffer (20 mM Tris-HCl, pH 7.5, 1.0M LiCl, 2 mM EDTA). Each time magnetic beads are separated using Magnetic Particle Concentrator (Dynal MPC™-S, Invitrogen Corporation, Carlsbad, Calif. Cat #120.20D).

After final wash the beads are resuspended in 30 ul of Binding buffer and mixed with 2.6 ul of capture 1 oligonucleotide #100003_19_polyA (26 pmole). Final reaction volume is brought to 45 ul final volume by adding water and 0.01% Tween 20, and incubated at room temperature with continuous rotation (~30-45 min). After incubation annealed magnetic beads are separated using Magnetic Particle Concentrator, supernatant is discarded. Magnetic beads subsequently are washed (3 times) with Washing buffer B (10 mM Tris-HCl, pH 7.5, 0.15M LiCl, 1 mM EDTA), washed once with Storage Buffer Oligo $(dT)_{25}$ (250 mM Tris-HCl, pH 7.5, 20 mM EDTA, 0.1% Tween-20, 0.02% $NaN_3$), resuspended in 30 ul of Storage Buffer Oligo $(dT)_{25}$, and kept at 4° C. for future use.

Example XIV

Binding of Target Agent and Removal of Excess DNA-Enzyme Conjugate (Model System Study)

A DNA Target Agent, oligonucleotide 100003_39 (39 nucleotides long) was synthesized using standard phosphoramidite chemistry (TriLink BioTechnologies, Inc. San Diego, Calif.) and is purified as described in Example XI.

5'-TGGACACACTCCCGATCACCACGATCTAGGTGTCATCCT-3'

Capture 2 oligonucleotide #100003_15_amino is conjugated to a Glucose Oxidase from *Aspergillus niger* (Fluka, 49180) according to the procedure for conjugation described in Example XI, or as an alternative, in Example XII Typically 0.15 mg/ml of the conjugate is obtained.

In parallel Capture 1 oligonucleotide immobilized-Oligo $(dT)_{25}$ magnetic beads is prepared according to the procedure for annealing described in Example XIII.

To reconstitute a model system 100 fmol of Target Agent, oligonucleotide 100003_39, is spiked into 1 ug of Human Genomic DNA (Clontech, Palo Alto, Calif. Cat #636401) along with 0.5 pmol of Capture 2 oligonucleotide-Glucose oxidase conjugate. Total reaction volume is 30 ul (6×SSPE, 0.01% Tween 20). The resulting reaction mixture is transferred into the tube containing 0.5 pmol of washed, dry Capture 1 oligonucleotide immobilized-Oligo $(dT)_{25}$ magnetic beads and gently mixed. Hybridization is carried at room temperature with continuous rotation for 1 hr.

Unbound Capture 2 oligonucleotide-Glucose oxidase conjugate is removed by washing (3 times) with 6×SSPE (0.9M NaCl, 60 mM $NaH_2PO_4$, 6 mM EDTA). Each time magnetic beads are separated using Magnetic Particle Concentrator (Dynal MPC™-S, Invitrogen Corporation, Carlsbad, Calif. Cat #120.20D). After the last wash the supernatant is carefully removed, remaining magnetic beads are resuspended in 10 ul of 2M Potassium Phosphate Buffer (pH 6.0) and kept at 4° C.

The Target Agent bound Capture 2 oligonucleotide-Glucose oxidase conjugate remains on the magnetic beads and is available for detection. In parallel, as a negative control, similar reaction is set up with no Target Agent spiked into 1 ug of Human Genomic DNA.

Example XV

Detection of DNA Target Agent Bound Magnetic Beads (Model System Study)

A DNA Target Agent bound magnetic beads is prepared according to the capture procedure described in Example XIV. Resulted 10 ul of Target Agent bound magnetic beads is washed (2 times) with 100 ul of 2M Potassium Phosphate Buffer (pH 6.0).

Each time magnetic beads are separated using Magnetic Particle Concentrator (Dynal MPC™-S, Invitrogen Corporation, Carlsbad, Calif. Cat #120.20D). After the last was the supernatant is carefully removed, remaining magnetic beads are resuspended in 2-5 ul of buffer containing 2M Potassium Phosphate Buffer (pH 6.0), 0.1 mM DCPIP (2,6-Dichloroindophelol, 0.1 ug/ul BSA).

In parallel a Detection Cell is assembled. Detection Cell contains 2 reaction chambers (anode and cathode reaction chambers; see, e.g., FIG. 44) separated by NAFION Membrane N-117 (FuelCellStore, San Diego, USA). Each reaction chamber has gold electrode inserted in it. Gold electrodes are connected to Fluke 289 True-RMS Industrial Logging Multimeter with TrendCapture (Fluke, Everett, Wash., USA) to take potentiometric or amperometric measurements.

20 ul of Working Buffer (2M Potassium Phosphate Buffer (pH 6.0), 0.1 mM DCPIP (2,6-Dichloroindophelol)) is added to each reaction chamber. 1 ul of Target bound magnetic beads is mixed with 1 ul of 1M glucose and transferred into anode reaction chamber (e.g., the top chamber in the device shown in FIG. 44). Potentiometric measurements are taken continuously or every 5 minutes of interval. Presence of the DNA Target Agent is detected by measurements of increasing potential (1-55 mV range).

During the measurements of the negative control reaction (no Target Agent; see Example XIV) no potential is detected.

Example XVI

Preparation of Antibody-Enzyme Conjugates

Capture Antibody 2, an anti-Mouse α-Human IL-8 Monoclonal Antibody (for ICC, BD Pharmingen cat #550419) is purified using NAP-5 column (0.1M/0.15M buffer of $NaHCO_3$/NaCl, pH 8.3), 0.5 ml loaded, 0.1 ml is pushed and 0.7 ml collected. Based on $A_{280}$ reading 0.45 mg/ml Mouse α-Human IL-8 Monoclonal Antibody recovery is observed.

Purified Capture Antibody 2 subsequently is chemically modified using Succinimidyl 4-formylbenzoate (C6-SFB). 660 ul of purified antibody and 30 ul of C6-SFB (20 mM in DMF) are mixed (1:40 ratio) and incubated at room temperature for 2 hrs. Reaction product is cleaned up using 5 ml HiTrap (GE) desalting column and 1.5 ml eluant is collected. Based on $A_{260}$ reading more than 80% recovery of Capture Antibody 2-C6-SFB is observed.

A Glucose Oxidase from *Aspergillus niger* (Fluka, 49180) is purified using NAP-5 column (1×PBS buffer, pH 7.2). 0.25 ml of Glucose Oxidase (5 mg/ml) is loaded on a column. After 0.25 ml push 1 ml of eluant is collected and quantified. Based on $A_{280}$ reading 1.25 mg/ml (7.8 uM) Glucose Oxidase recovery is observed.

Purified Glucose Oxidase subsequently is chemically modified using Succinimidyl 4-hydrazinonicotionate acetone hydrazone (C6-SANH). 950 ul of 7.8 uM of Glucose Oxidase and 10.4 ul of C6-SANH (10 mM in DMF) are mixed (1:20 ratio) and incubated at room temperature for 30 min. Reaction product is cleaned up using 5 ml HiTrap (GE) desalting column and 1.25 ml eluant is collected. BCA/BSA (BCA assay from Pierce, cat #23225/23227; Bradford assay from Pierce, cat #23236) assay is used to determine the concentration of recovered Glucose Oxidase-C6-SANH (typically ~1 mg/ml).

The conjugation of Glucose Oxidase and Capture Antibody 2 is typically achieved by mixing the 500 ul of Glucose Oxidase-C6-SANH and 750 ul of Capture Antibody 2-C6-SFB in a molar ratio 3:1 and incubated overnight at room temperature. The resulting conjugates are analyzed on TBE/UREA gel, and purified using MiniQ FPLC.

Standard gradient approach is utilized using MiniQ 4.6/50 PE column (GE Healthcare, cat #17-5177-01), 0.25 ml/min flow rate, detection at 280 nm. buffer A: 20 mM Tris/HCl, pH 8.1, buffer B: 20 mM Tris/HCl, NaCl 1M, pH 8.1. BCA/BSA assay is used to determine the concentration of recovered Glucose Oxidase-Capture Antibody 2 (~3 ml of eluant, 0.1 mg/ml).

Example XVII

Preparation of Antibody Immobilized Magnetic Beads

Capture Antibody 1, an anti-Mouse α-Human IL-8 Monoclonal Antibody (ELISA capture, BD Pharmingen cat #554716) is purified using NAP-5 column (0.1M/0.15M buffer of $NaHCO_3$/NaCl, pH 8.3), 0.5 ml loaded, 0.1 ml is pushed and 0.7 ml collected. Based on $A_{280}$ reading 0.45 mg/ml Mouse α-Human IL-8 Monoclonal Antibody recovery is observed.

In parallel primary amino-derivatized magnetic beads (Dynabeads® M-270 Amine, Invitrogen Corporation, Carlsbad, Calif. Cat #610). is activated with water soluble homobifunctional NHS(N-hydroxy-succinimidyl)-ester according to the manufacturer's instruction. Briefly, magnetic beads is resuspended in 0.1M sodium phosphate buffer with 0.15M NaCl, pH 7.4.

NHS-ester, DTSSP (3,3'-Dithiobissulfosiccinimidylpropionate) (Pierce, Rockford, Ill., USA; Cat #21578), is dissolved in water and added directly to the beads. Final volume is equal to the bead-volume originally pipetted from the vial. Reaction is mixed, and incubated 30 min at room temperature with slow tilt rotation. After incubation, the tube is placed on the Magnetic Particle Concentrator (Dynal MPC™-S, Invitrogen Corporation, Carlsbad, Calif. Cat #120.20D) for 4 min and supernatant is removed. Magnetic beads washed 2 more times with the buffer above. Finally NHS-ester activated magnetic beads is sequentially washed with ice-cold 1 mM HCl and ice-cold water. Then 0.7 ml Capture Antibody 1 is added and incubated for 2 hrs at 4° C. with slow tilt rotation. (Usually 10-fold molar excess of NHS-ester crosslinker is used compared to the amount of antibody to be immobilized. For antibody coating of Dynabeads® M-270 Amine, 3 ug pure antibody per $10^7$ beads and final concentration of $1-2 \times 10^9$ beads per ml is recommended).

After incubation, tube is placed on the Magnetic Particle Concentrator for 4 min and supernatant is removed. 0.05M Tris pH7 is added and incubated for 15 min at room temperature with slow tilt rotation, to quench non-reacted groups.

Magnetic beads washed 4 times in buffer containing PBS and 0.5% BSA. After the final wash the coated beads is resuspended in PBS and 0.1% BSA to 1 $10^9$ beads/ml. For storage of the Capture Antibody 1 coated magnetic beads 0.02% sodium azide is added and kept at 4° C.

Example XVIII

Binding of Target Agent and Removal of Excess Antibody-Enzyme Conjugate (Model System Study)

Capture Antibody 2, an anti-Mouse α-Human IL-8 Monoclonal Antibody (for ICC, BD Pharmingen cat #550419) is conjugated to a Glucose Oxidase from *Aspergillus niger* (Fluka, 49180) according to the procedure for conjugation described in Example XVI. Capture Antibody 1, an anti-Mouse α-Human IL-8 Monoclonal Antibody (ELISA capture, BD Pharmingen cat #554716) immobilized aminoderivatized magnetic beads (Dynabeads® M-270 Amine, Invitrogen Corporation, Carlsbad, Calif. Cat #610) is prepared according to the procedure for immobilization described in Example XVII.

Above mentioned monoclonal antibodies represent a pair recognizing two different epitopes of recombinant Human IL-8.

To reconstitute a model system 0.5 ug of Protein Target Agent, recombinant Human IL-8 (BD Pharmingen cat #554609, 0.1 mg/ml) is spiked into FBS (Fetal Bovine Serum) along with Capture Antibody 2—Glucose Oxidase conjugate (typically 20 ug is used).

15 ug (30 ul) of Capture Antibody 1 immobilized magnetic beads is blocked by mixing with Fetal Bovine Serum for 45 min at room temperature. The resulting reaction mixture is placed on the Magnetic Particle Concentrator and supernatant is discarded.

Above mentioned reconstituted model system (Human IL-8 and Capture Antibody 2—Glucose Oxidase conjugate) is added to the washed Capture Antibody 1—magnetic beads and the volume of reaction mixture is brought to 500 ul with PBS.

The reaction mixture, after adding to it BSA to a final concentration of 1 mg/ml, is incubated at room temperature with slow tilt rotation.

Unbound Capture Antibody 2—Glucose Oxidase conjugate is removed by washing with PBS (7 times). After the last wash the supernatant is carefully removed, remaining magnetic beads are resuspended in 10 ul of 2M Potassium Phosphate Buffer (pH 6.0) and kept at 4° C.

The Target Agent bound Capture Antibody 2—Glucose oxidase conjugate remains on the magnetic beads and is available for detection.

In parallel, as a negative control, similar reaction is set up with no Target Agent (Human IL-8) spiked into FBS (Fetal Bovine Serum).

Example XIX

Detection of Protein Target Agent Bound Magnetic Beads (Model System Study)

A Protein Target Agent bound magnetic beads is prepared according to the capture procedure described in Example XVIII. Resulted 10 ul of Target Agent bound magnetic beads is washed (2 times) with 100 ul of 2M Potassium Phosphate Buffer (pH 6.0).

Each time magnetic beads are separated using Magnetic Particle Concentrator (Dynal MPC™-S, Invitrogen Corporation, Carlsbad, Calif. Cat #120.20D). After the last was the supernatant is carefully removed, remaining magnetic beads are resuspended in 2-5 ul of buffer containing 2M Potassium Phosphate Buffer (pH 6.0), 0.1 mM DCPIP (2,6-Dichloroindophelol, 0.1 ug/ul BSA).

In parallel a Detection Cell is assembled. Detection Cell contains 2 reaction chambers (anode and cathode reaction chambers; see, e.g., FIG. 44) separated by NAFION Membrane N-117 (FuelCellStore, San Diego, USA).

Each reaction chamber has gold electrode inserted in it. Gold electrodes are connected to Fluke 289 True-RMS Industrial Logging Multimeter with TrendCapture (Fluke, Everett, Wash., USA) to take potentiometric or amperometric measurements.

20 ul of Working Buffer (2M Potassium Phosphate Buffer (pH 6.0), 0.1 mM DCPIP (2,6-Dichloroindophelol)) is added to each reaction chamber. 1 ul of Target bound magnetic beads is mixed with 1 ul of 1M glucose and transferred into anode reaction chamber. Potentiometric measurements are taken continuously or every 5 minutes of interval. Presence of the Protein Target Agent is detected by measurements of increasing potential (1-55 mV range).

During the measurements of the negative control reaction (no Target Agent; see Example XVIII) no potential is detected.

Specific Operating Embodiment

Further information regarding the performance of this invention may be had by discussion of basic reagents and procedures of this invention. Like each of the examples discussed above, it relies on the generation of electric potential, which can be detected by the working cell of the portable test unit of the invention. That test unit can accept a test module (disposable) which comprises an membrane, or a membrane free measurement chamber. In a preferred embodiment, the test chamber is a plastic well which is supported on a vertical flange on which are painted the two electrodes, separated by an operative distance across which a potential can be measured by closing a circuit. The electrodes can be painted on the test chamber backing, and may be preferably be made of gold. In a preferred embodiment, the cathode is overlaid with a film of Nafion of similar polymeric material.

Reagents & Testing Procedures

A. Reagents. The following reagents are the standard reagents used in the SASP testing. All reagents are commercially available. The time needed for sample prep (using standard molecular biology techniques) accounts for 95% of the time needed to complete the detection assay. Optimization of the sample prep through automation and robotics can significantly reduce the duration of the assay. Oligonucleotides and other listed nucleic acid sequences intended for use as model/control reagents.

1. First Complexing ("FC") oligonucleotide #100003_19_polyA (36 nucleotides):

5'-GTGATCGGGAGTGTGTCCAAAAAAAAAAAAAAAAA-3'

Second Complexing ("SC") oligonucleotide #100003_15_amino (5'-NH$_2$modified 15 nucleotides):

5'-AGGATGACACCTAGA-3'

Target Specific ("TS") oligonucleotide 100003_39 (39 nucleotides)

5'-TGGACACACTCCCGATCACCACGATCTAGGTGTCATCCT-3'

Dynabeads® Oligo (dT)$_{25}$ magnetic beads
Dynabeads® M-270 Amine
Dynal MPC™-S Magnetic Particle Concentrator
Glucose Oxidase from *Aspergillus niger*
D-glucose
DCPIP (2,6-Dichlorophenolindophenol)
Lightning-Link Glucose Oxidase Congugation Kit
Human Genomic DNA
ssM13mp18
NAFION Membrane N-117
Liquid Nafion, LIQGUION™ Solution All other chemicals and materials, necessary to make standard buffers and solutions, were purchased from Sigma-Aldrich, Pierce Biotechnologies and/or VWR.

Standard Buffers:

1. 1× Binding Buffer (20 mM Tris-HCl, pH 7.5, 1.0M LiCl, 2 mM EDTA).

2. Washing buffer B (10 mM Tris-HCl, pH 7.5, 0.15M LiCl, 1 mM EDTA).

3. Storage Buffer (250 mM Tris-HCl, pH 7.5, 20 mM EDTA, 0.1% Tween-20, 0.02% NaN$_3$).

B. Testing Procedure. The following description is provided for a "two-step" hybridization. It has however, been empirically determined that a one-step hybridization (i.e., performing the hybridization steps in a single reaction vessel) can beneficial.

1. Experimental Setup
   a. FC oligonucleotide is purified using NAP-5 column (0.1M/0.15M buffer of NaHCO$_3$/NaCl, pH 8.3). following the manufacturers protocol. Briefly, 0.2 ml of 100 uM water solution of oligonucleotide #100003_15_amino is loaded on a column. After 0.3 ml push 0.8 ml of eluant is collected and quantified. Based on $A_{260}$ reading more than 90% of recovery should be observed.

b. Purified FC oligonucleotide is annealed with Oligo (dT)$_{25}$ magnetic beads.

c. 30 ul of the foregoing magnetic beads suspension is washed twice with 1× Binding Buffer (20 mM Tris-HCl, pH 7.5, 1.0M LiCl, 2 mM EDTA). Magnetic beads are separated using a magnetic particle concentrator following each wash.

d. Following final wash the beads are resuspended in 30 ul of Binding Buffer and mixed with 2.6 ul of FC oligonucleotide (26 pmole). The final reaction volume is adjusted to 45 ul final volume by the addition of DDI water/0.01% Tween 20, and incubated at room temperature with continuous rotation (~30-45 min).

e. Following incubation the annealed magnetic beads are separated using a magnetic particle concentrator and the supernatant is discarded. The Magnetic beads are washed (3 times) with Washing buffer B (10 mM Tris-HCl, pH 7.5, 0.15M LiCl, 1 mM EDTA), washed once with Storage Buffer Oligo (dT)$_{25}$ (250 mM Tris-HCl, pH 7.5, 20 mM EDTA, 0.1% Tween-20, 0.02% NaN$_3$), and resuspended in 30 ul of Storage Buffer Oligo (dT)$_{25}$. The final solution can be stored at 4° C. for future use.

2. Test Cell Conditioning

The test cell is pre-conditioned to remove positive background by washing the cell with dH20 (10×50 ul) followed by "shorting" the cell (accomplished via scripting) for 120 seconds.

3. Sample Assaying a. The SC oligonucleotide is purified using the same basic protocol as set forth above for the FC oligonucleotide. Purified SC oligonucleotide is conjugated with Glucose Oxidase using the commercially available Lightning-Link Glucose Oxidase Congugation Kit pursuant to the manufacturer's recommended protocol with minor modifications. Briefly, 4 ul of the modifier is added to 40 ul of amino-modified SC oligonucleotide (50 uM in water). The resulting solution is admixed with ½ vial of LL-Gox and incubated overnight in the absence of ambient light and at room temperature. Following overnight incubation, 5 ul of quencher is added to the reaction mixture and incubated for 30 min in the absence of ambient light at room temperature.

b. The resulting conjugate is purified by centrifugation through a Micron YM-100 spin column (Millipore, USA) to remove unreacted amino modified oligonucleotide. For best results, 50 ul of the resulting conjugate is loaded onto the column and centrifuged at 8000 rpm for 8 min. Flow through is discarded and 200 ul of 1× (50 mM) PBS (50 mM, pH 7.5) is added to the column and centrifuged at 8000 rpm for 8 min. The flow through is once again discarded and 50 ul of 1×PBS (50 mM, pH 7.5) is added to a column, carefully mixed using a vortex for 5-10 seconds, followed by centrifugation at 2000 rpm for 2 min. The resulting 50 ul of purified SC oligo-Enzyme conjugate is collected and can be stored at 4° C. for future use.

c. TS oligonucleotide is purified in a manner similar to that described above for the FC and SC oligonucleotides.

d. TS oligonucleotide (0.5-100 fmol) is added to 1 ug of Human Genomic DNA (or ssM13 mp18 plasmid DNA) with 0.5 pmol of Conjugate. The total reaction volume should be approximately 30 ul (6×SSPE, 0.01% Tween 20). The resulting reaction mixture is transferred into a tube containing 0.5 pmol of washed, dry FC immobilized-Oligo (dT)$_{25}$ magnetic beads and gently mixed. Hybridization is conducted at room temperature with continuous rotation for 1 hr.

e. With the magnetic field in place, unbound Conjugate is removed by washing (3 times) with 6×SSPE (0.9M NaCl, 60 mM NaH$_2$PO$_4$, 6 mM EDTA). Following washing, the supernatant is carefully removed by pipetting and the Target-magnetic bead complex ("Complex") washed (2 times) with 100 ul of 2M Potassium Phosphate Buffer (pH 6.0) and resuspended in 2-5 ul of buffer containing 2M Potassium Phosphate Buffer (pH 6.0), 0.1 mM DCPIP (2,6-Dichloroindophelol, 0.1 ug/ul BSA).

f. In parallel with the foregoing steps, a negative control is prepared wherein the reaction is performed without the inclusion of the TS oligo and Human Genomic DNA (or ssM13mp18 plasmid DNA).

g. Using the Detection Cell (type 1), 30 ul of Working Buffer (2M Potassium Phosphate Buffer (pH 6.0), 0.1 mM DCPIP (2,6-dichloroindophenol) is added to each (anode and cathode) reaction chamber. To assay for the presence (or absence) of the target species, 1 ul of the Complex and 1 ul of 1M glucose are added to the anode reaction chamber and thoroughly mixed.

h. The reaction is allowed to incubate for 5 min, after which measurements are taken continuously or every 30-180 seconds of interval. The presence of the target species is represented by signals of increasing potential (0.4-2.2V range). (see, representative output FIG. 2, below).

Apparatus Optimized For Portable Use

As noted, the assays made possible by this invention are susceptible of practice in a wide variety of apparatus. Particularly desirable apparatus will be portable, for deployment in the field. One such apparatus is described, by way of exemplification rather than limitation, below. Alternatives will occur to those of skill in the art without the exercise of inventive faculty.

The Chemical Demonstration Unit Workstation Software controls timing and recording of measurements. This document only describes the workstation software and not the complete system. The PC workstation is connected via USB to a Data Acquisition board (Data Acquisition DT9812). The board controls reading to the Amplifier circuitry using the digital outputs, and analog inputs. The circuitry is connected to the Chemistry Cell Cartridge where the GOX Cell is housed.

There a variety of functional requirements or tasks the workstation of this invention must satisfy. These include Control of the Amplifier circuitry Use the Digital out of the Data Acquisition board to setup and measure Time the Digital output to get measurements at specified times Measurement Take initial baseline measurements Take Cell measurement at defined time(s)

Calculate actual measurement using baseline measurement Display

The workstation should prompt the user to perform required actions to synchronize with the measurement activity. e.g. insert Chemistry Cell Cartridge.

The workstation should display continuous and period measurement data Data

Baseline data must be preserved and recorded to get corrected data.

Complete run data should be persisted and easily retrievable.

The needs of the invention are met by a portable system that relies on a combination of hardware and software to deliver a clear, reliable signal. The current version is being developed with dotNet 2.0 using Microsoft Visual Studio 2005.

The workstation currently uses the Data Translation DT9812 data acquisition board connected via standard USB 2.0. Data Translation provides Windows XP drivers as well as a dotNet API library. The circuit board makes use of the DT9812 digital outputs for controlling the switches on the circuit, and uses the DT9812's analog input for voltage measurements.

Installation Procedure

The installation and use of the workstation requires specific functionalities. First the workstation preferably needs to be running Windows XP with Service Pack 2. Windows dotNET Version 2.0 preferably needs to be installed. Data Translation provides a CD containing the Windows Drivers and the dotNET API, both need be installed first. Then DT9812 needs to be plugged in next for the system to recognize the device and use the installed drivers. For internal development use, the latest version of the workstation will be checked for on the intranet website codequest: 8080/apps/Box331. Other installations will have different installation procedures.

Reference is made to U.S. Provisional Patent Application Ser. No. 60/834,951, filed Aug. 2, 2006; U.S. Provisional Patent Application Ser. No. 60/851,697, filed Oct. 13, 2006; U.S. Provisional Patent Application Ser. No. 60/853,697, filed Oct. 23, 2006; U.S. Provisional Patent Application Ser. No. 60/859,441, filed Nov. 16, 2006; U.S. Provisional Patent Application Ser. No. 60/874,291, filed Dec. 12, 2006; U.S. Provisional Patent Application Ser. No. 60/876,279, filed Dec. 21, 2006; and U.S. patent application Ser. No. 11/703,103, filed Feb. 7, 2007, each of which are herein incorporated by reference in their entireties for all purposes.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An assay system for the detection of a target in a liquid sample, wherein said assay system comprises:
   a first capture moiety which binds to any target present in said sample, said first capture moiety complexed with a redox reaction enzyme;
   a substrate recognized by said enzyme, which substrate, when acted upon by said enzyme, releases electrons; and
   an electronic circuit for self-actuating signal producing detection of electric potential or current developed by the release of electrons from said substrate when digested by said enzyme, wherein said electric potential or current is detected in the absence of any source of electrical power provided to said system other than the electrical power generated by the release of electrons from said substrate when digested by said enzyme.

2. The assay system of claim 1, wherein said circuit detects the presence of said electric potential or current directly.

3. The assay system of claim 1, wherein said circuit specifically detects directly said released electrons.

* * * * *